(12) United States Patent
Woodman et al.

(10) Patent No.: US 8,063,019 B2
(45) Date of Patent: Nov. 22, 2011

(54) SCAFFOLD POLYPEPTIDES FOR HETEROLOGOUS PEPTIDE DISPLAY

(75) Inventors: Robbie Woodman, Paris (FR); Johannes Tsung-Han Yeh, Boston, MA (US); Sophie Laurenson, Dartford (GB); Paul Ko Ferrigno, Leeds (GB)

(73) Assignee: Medical Research Council, London (GB)

(*) Notice: Subject to any disclaimer, the term of this patent is extended or adjusted under 35 U.S.C. 154(b) by 450 days.

(21) Appl. No.: 11/917,057

(22) PCT Filed: Jun. 8, 2006

(86) PCT No.: PCT/GB2006/002115
§ 371 (c)(1),
(2), (4) Date: Dec. 10, 2007

(87) PCT Pub. No.: WO2006/131749
PCT Pub. Date: Dec. 14, 2006

(65) Prior Publication Data
US 2008/0207509 A1    Aug. 28, 2008

(30) Foreign Application Priority Data

Jun. 10, 2005 (GB) .................................. 0511873.2
May 4, 2006 (GB) .................................. 0608836.3

(51) Int. Cl.
*A61K 38/16* (2006.01)
*C07K 14/00* (2006.01)
(52) U.S. Cl. .......................................... 514/12; 530/300
(58) Field of Classification Search .................. None
See application file for complete search history.

(56) References Cited

U.S. PATENT DOCUMENTS 6,680,424 B2 * 1/2004 Atkinson et al. .............. 800/279

FOREIGN PATENT DOCUMENTS

| WO | 00/05406 | 2/2000 |
| WO | 2005/046709 | 5/2005 |

OTHER PUBLICATIONS

Pavlova et at., The role of the second binding loop of the cysteine protease inhibitor, cystatin A (stefin A), in stabilizing complexes with target proteases is exerted predominantly by Leu73. Eur. J. Biochem. 269 (22):5649-5658, 2002.*

Machleidt, W. et al., Biomedica Biochimica Acta, 50:613-620 (1991). "Molecular mechanism of inhibition of cysteine proteinases by their protein inhibitors: Kinetic studies with natural and recombinant variants of crystatins and stefins."
Shibuya, K. et al., Journal of Biochemistry, 118:635-642 (1995). "Significance of the highly conserved Gly-4 residue in human cystatin A."
Skerra, A., Current Opinion in Chemical Biology, 7:683-693 (2003). "Imitating the humoral immune response."
Database EMBL [Online], "Human Radiated Keratinocyte mRNA for Cysteine Protease Inhibitor" XP002409648 retrieved from EBI accession No. EM_PRO:X05978, Database accession No. X05978, Apr. 2, 1988.
Arana, David M et al: "The pbs2 map kinase kinase is essential for the oxidative-stress response in the fungal pathogen *Candida albicans*" Microbiology vol. 151, Apr. 2005, pp. 1033-1049.
Borghouts, C et al: "Peptide aptamers: recent developments for cancer therapy" Expert Opinion on Biological Therapy, Ashley, London, GB, vol. 5, No. 6, Jun. 1, 2005, pp. 783-797.
Lupetti, Antonella et al: "Antimicrobial peptides: therapeutic potential for the treatment of candida infections." Expert Opinion on Investigational Drugs, vol. 11, No. 2, Feb. 2002, pp. 309-318.
Martin, J R et al: "The three-dimensional solution structure of human stefin A" Journal of Molecular Biology, Feb. 17, 1995, vol. 246, No. 2, pp. 331-343.
Woodman et al: "Design and validation of a neutral protein scaffold for the presentation of peptide aptamers" Journal of Molecular Biology, London, GB, vol. 352, No. 5, Oct. 7, 2005, pp. 1118-1133.
Zarrinpar A et al: "Optimization of specificity in a cellular protein interaction network by negative selection" Nature Dec. 11, 2003 United Kingdom, vol. 426, No. 6967, pp. 676-680.
Zarrinpar Ali et al: "Sho1 and pbs2 act as coscaffolds linking components in the yeast high osmolarity map kinase pathway" Molecular Cell Jun. 18, 2004, vol. 14, No. 6, pp. 825-832.

* cited by examiner

*Primary Examiner* — Ruixiang Li
(74) *Attorney, Agent, or Firm* — Nixon Peabody LLP

(57) ABSTRACT

The present invention relates to the use of Stefin A as a scaffold protein for the display of inserted peptides, particularly wherein the Stefin A is a human Stefin A. Several mutations are advantageously made in the wild type stefin A sequence to improve it as a scaffold; preferably the Stefin A comprises a heterologous peptide insertion at the Leu 73 site. Furthermore, preferably the scaffold protein comprises a V48D mutation; preferably the scaffold protein comprises a G4W mutation. Preferably the scaffold comprises Leu73, V48D and G4W mutations. The invention also relates to the scaffold proteins themselves, in particular a stefin A polypeptide having the Leu73, V48D and G4W mutations, such as shown as SEQ ID NO: 1. The invention also relates to a method for identifying binding proteins and to peptide A (RLNKPLPSLPV) and its use in treating yeast infections.

5 Claims, 15 Drawing Sheets

Figure 2
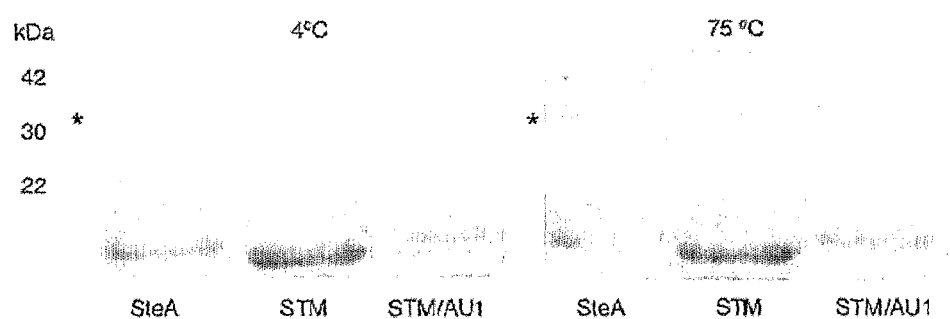
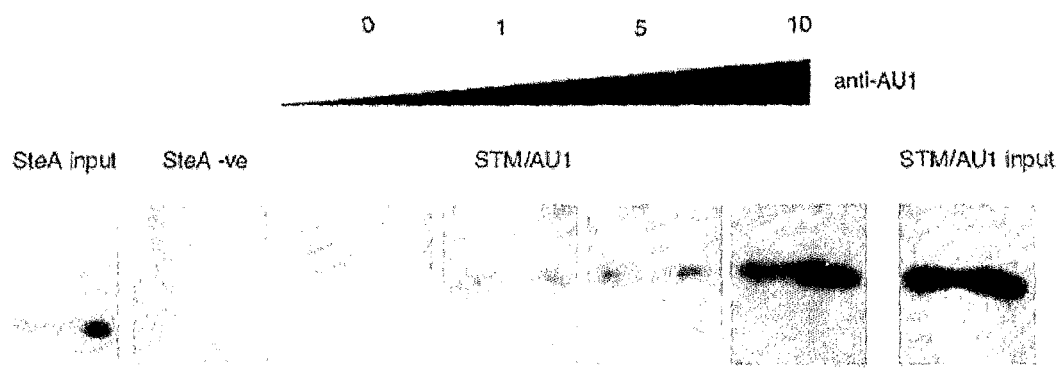

Figure 3
a
· · · · · ·  SteA
· · · · · ·  SteA heat treated
———  STM/AU1
———  STM/AU1 heat treated
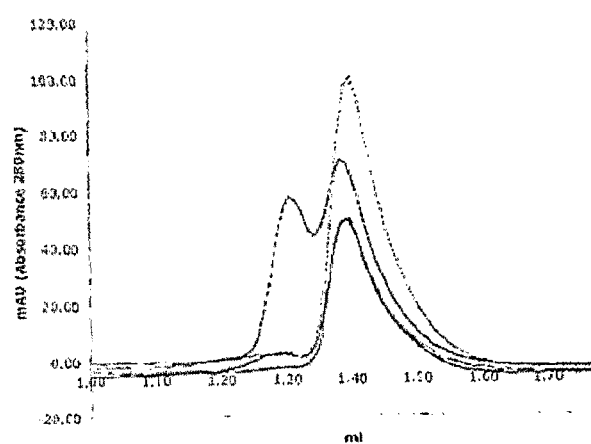
b
———  SteA 25°C
        SteA 50°C
        STM/AU1 25°C
· · · · · ·  STM/AU1 50°C
———  STM/AU1 97°C
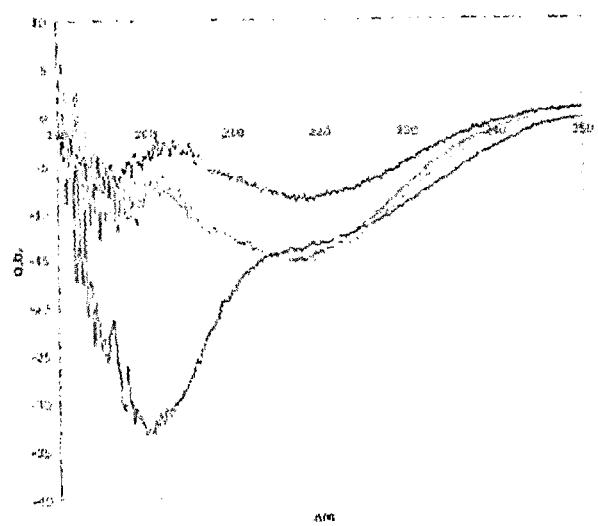

Figure 7 A.
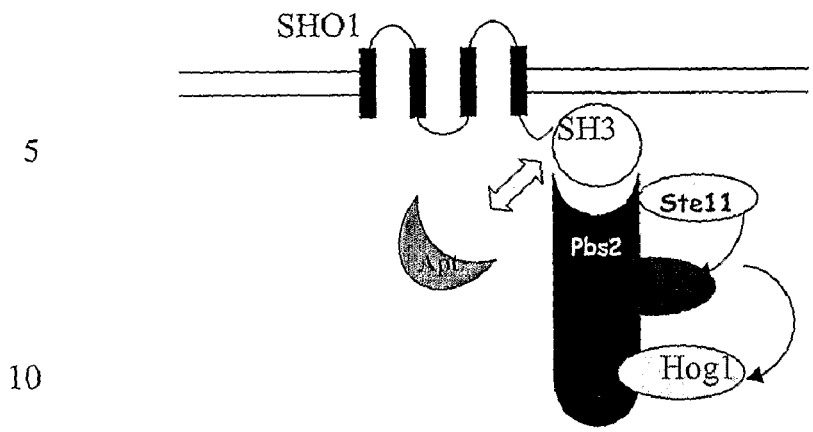
Figure 7 B.
1 M NaCl
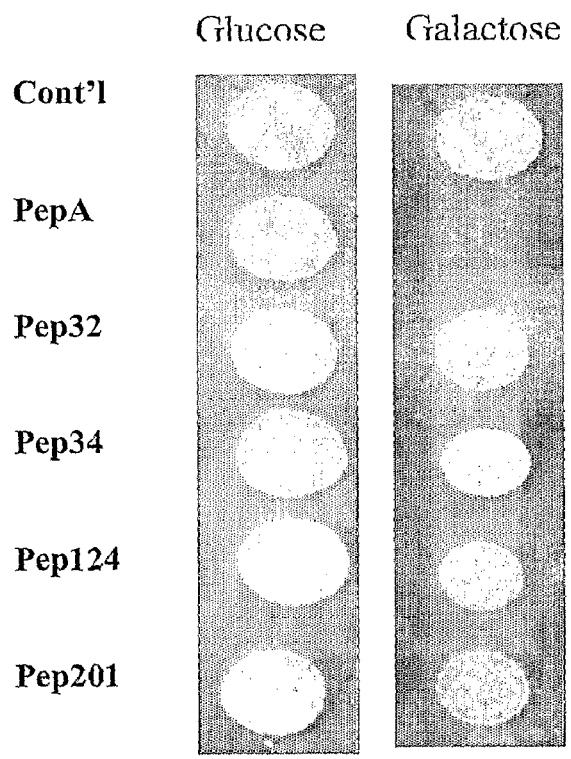

Figure 7 C.
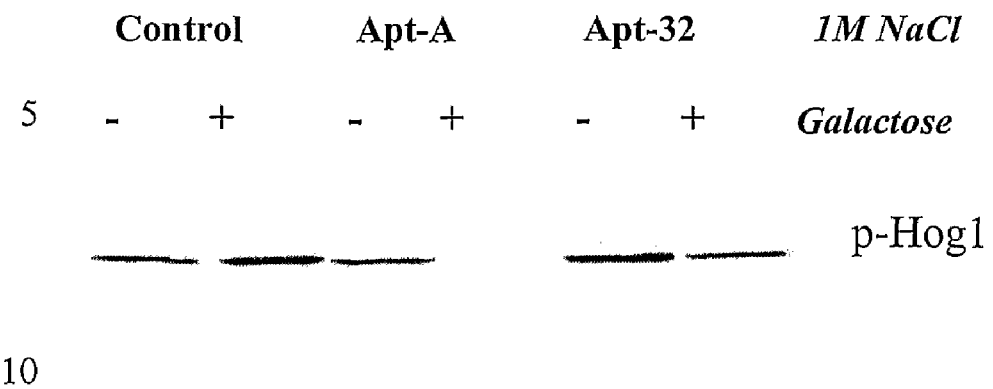
Figure 7 D.
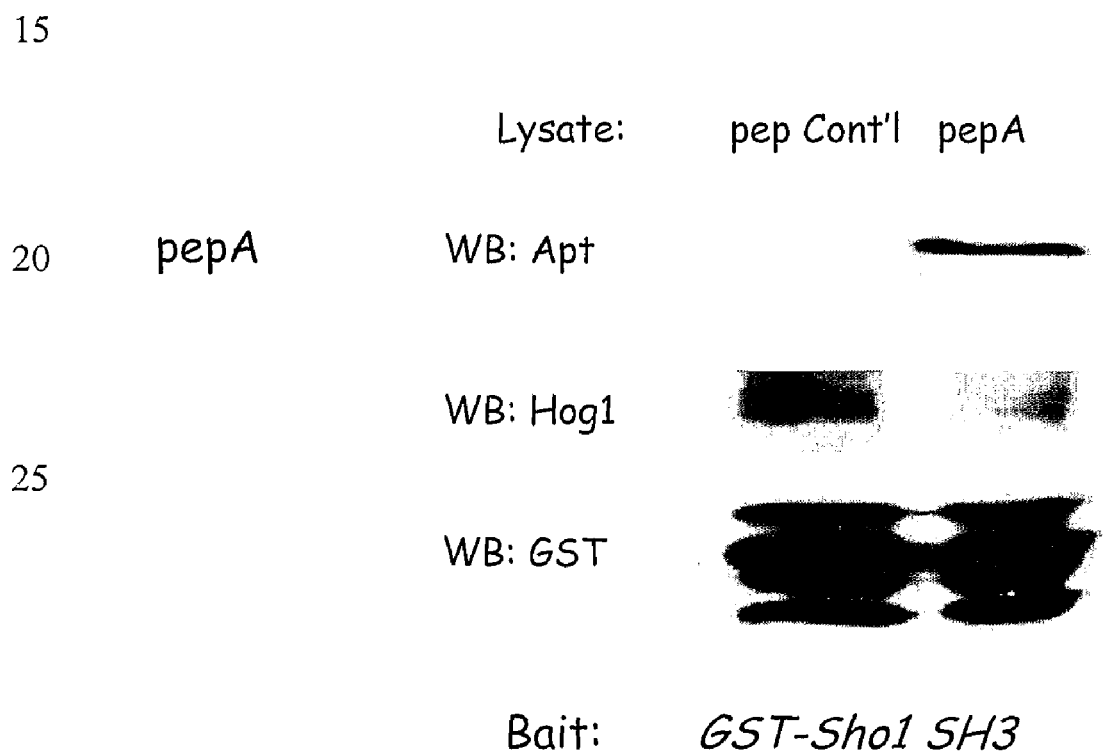

a c-Raf    252    SLSQRST<u>S</u>TPNVHM    265

Insert    *gp*SLSQRST<u>S</u>TPNVHM*gp*

Figure 9
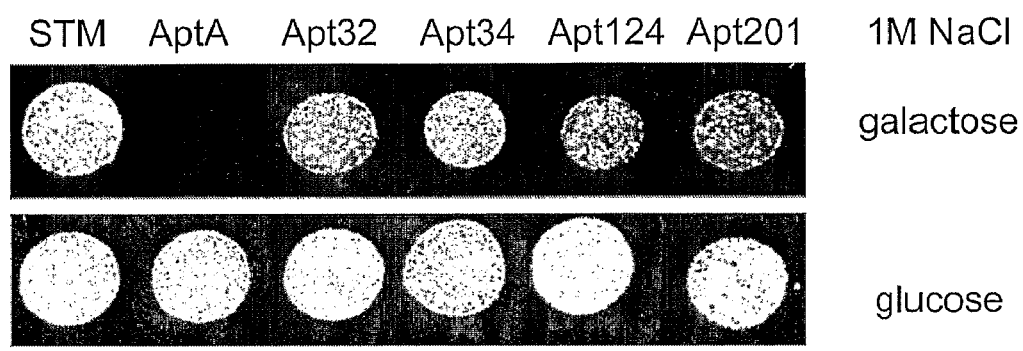
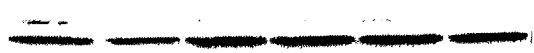

Figure 11
A.
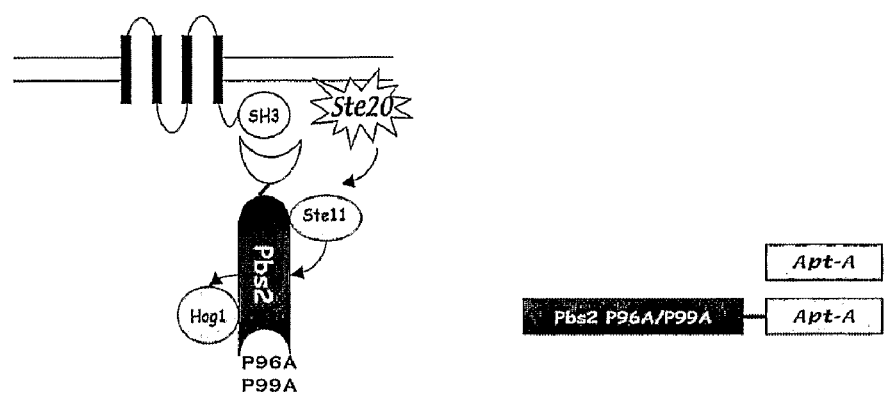
B.
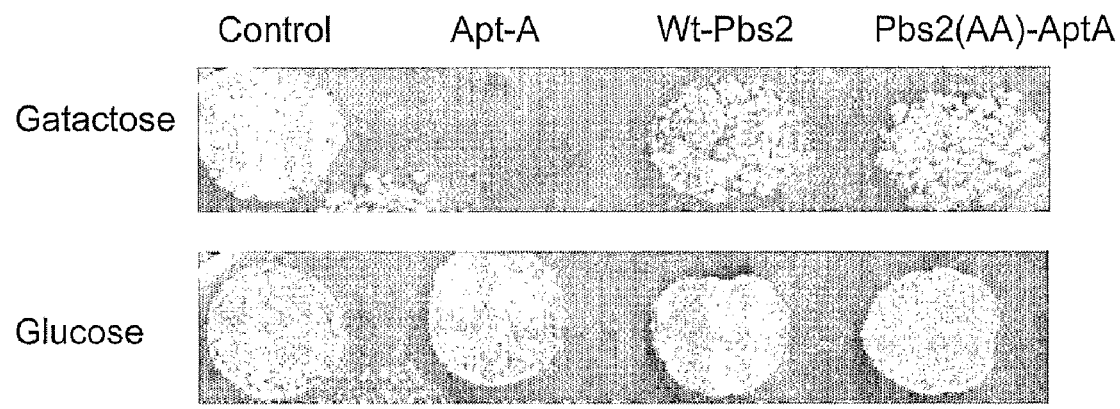

Figure 12
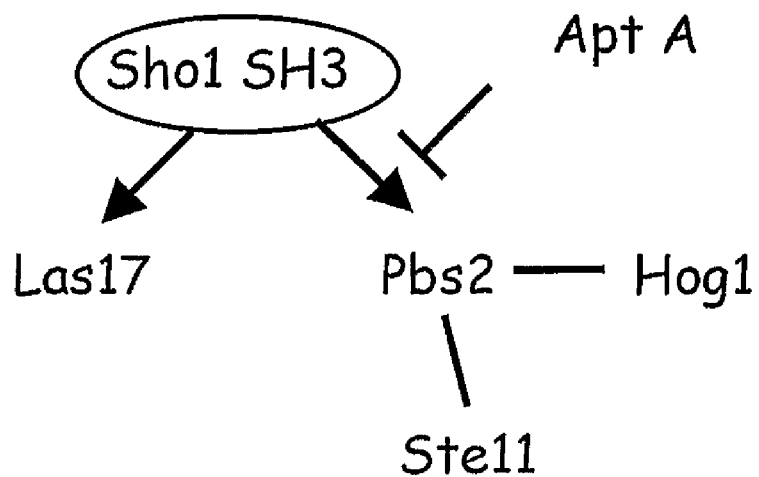
| Lysate: | STM | AptA |
|---|---|---|
| αSTM | |  |
| αHog1 |  | |
| αGST |  | |￼
| Bait: | GST-Sho1 SH3 | | ns.
SCAFFOLD POLYPEPTIDES FOR HETEROLOGOUS PEPTIDE DISPLAY

SEQUENCE LISTING

The instant application contains a Sequence Listing which has been submitted in ASCII format via EFS-Web and is hereby incorporated by reference in its entirety. Said ASCII copy, created on Nov. 17, 2010, is named 044195US.txt and is 44,449 bytes in size.

FIELD OF THE INVENTION

The present invention relates to scaffold proteins for display of peptides such as peptide aptamers. In particular, the invention relates to the use of stefin A as a scaffold protein, and to modified stefin A polypeptides for use as scaffold proteins.

BACKGROUND TO THE INVENTION

Study of protein interactions is central to an understanding of the biological roles of gene products in vivo. There are numerous ways of analysing or dissecting polypeptide interactions, and one of the most powerful is by use of peptide aptamers and study of their behaviour. Peptides and peptide aptamers may be used free in solution. However, small peptides when unconstrained will tend to form structures which present a limited interaction surface. Furthermore, they will often lose conformational entropy upon association with target molecules, reducing free energy of binding and consequently free peptides will often not form tight non-covalent complexes, which is a problem.

Rather than being used in free solutions, peptides of interest may be bound to physical supports, or displayed in the context of a larger polypeptide. It is display in the context of a polypeptide which is important in the present invention. Such display is often brought about using scaffold proteins.

Engineered protein scaffolds for molecular recognition have been produced and used in the prior art. For example, Skerra (2003 Curr Opin Chem Biol. vol. 7 pages 683-93) discusses scaffolds used for the generation of artificial receptor proteins with defined specificites. According to Skerra, the best scaffolds should have robust architecture, small size, be monomeric, be susceptible to protein engineering (eg. fusion proteins) and have a low degree of post-translational modification. Furthermore, the most advantageous scaffolds should be easy to express in host cells (usually prokaryotic cells in the prior art), have a region susceptible to insertion or replacement of amino acids to create novel binding sites, and such insertion/replacement of binding sites should not affect folding of the scaffold.

The most commonly used scaffolds are based on the framework regions of immunoglobulin or 'antibody' chains. In particular, the Ig framework and/or shortened or fused versions of it have been used to present and geometrically constrain peptides in the prior art. However, antibodies are large, and even the recombinant fragments are of considerable size (eg. Fab fragments are about 450aa, and even scFv fragments are about 270aa). This makes them awkward to manipulate in vitro and in vivo. Furthermore, they are comprised of two different polypeptide chains which are unstable in the sense of dissociation, oligomerisation and even wholesale aggregation, which represent further problems associated with their use.

Prior art scaffolds have included inactivated staphylococcal nuclease, green fluorescent protein (GFP) and thioredoxin A (TrxA), as well as isolated protein folds such as the Z domain of staphylococcal protein A, "affibodies", anticalins, and ankyrin repeats. Further prior art scaffold proteins include the fibronectin type III domain ('Fn3'), lipocalin family proteins from which anticalins are derived, bilin binding protein (BBP), and others.

This technology has been most actively pursued using bacterial thioredoxin (TrxA) as a scaffold. However, there are problems associated with TrxA. For example, E. coli TrxA can inhibit apoptosis which may lead to confounding observations in cell-based assays. Also, the two cysteine residues which border inserted peptides, and which form a reversible disulphide bond in TrxA, can lead to uncertainty regarding the "correct" state for presentation of active peptide.

The present invention seeks to overcome problem(s) associated with the prior art.

SUMMARY OF THE INVENTION

The present invention is based upon a detailed understanding of the molecular biology of the Stefin A protein (sometimes referred to as 'Cystatin A'). This understanding has allowed modification of the wild type SteA protein into a form rendering it suitable for use as a scaffold protein. Scaffold proteins based on Stefin A have several advantages over prior art scaffolds.

According to the present invention, Stefin A has been advantageously rendered biologically neutral. As is explained in more detail below, rational mutations have been introduced into sites in the Stefin A polypeptide which ablate its biologically significant interactions and activities. Furthermore, an insertion site has been chosen and experimentally demonstrated to be able to accept and constrain inserted peptides such as the peptide aptamers used in some of the examples below. Furthermore, two further discrete solvent exposed surfaces of Stefin A have been rationally selected by the inventors which advantageously provide the opportunity to select peptide binding partners with increased avidity and/or increased specificity for the target peptide.

Thus the invention provides the use of Stefin A as a scaffold protein, and provides modified Stefin A polypeptides which are useful as scaffold proteins. Preferably the Stefin A is a human Stefin A.

In another aspect the invention relates to a use as described above wherein the Stefin A comprises a heterologous peptide insertion at the Leu 73 site.

In another aspect the invention relates to a use as described above wherein the scaffold protein comprises a V48D mutation.

In another aspect the invention relates to a use as described above wherein the scaffold protein comprises a G4W mutation.

In another aspect the invention relates to a use as described above wherein the Stefin A comprises a heterologous peptide insertion at the Leu 73 site and further comprises the V48D and G4W mutations.

In another aspect the invention relates to a use as described above wherein the scaffold protein comprises the sequence shown as SEQ ID NO: 1. This is the preferred triple mutant scaffold sequence.

In another aspect the invention relates to a use as described above wherein the scaffold protein comprises the sequence shown as SEQ ID NO:3 and the sequence shown as SEQ ID NO:4. These are the preferred STM sequences each side of the preferred Leu73 insertion site.

In another aspect the invention relates to a polypeptide comprising the amino acid sequence shown as SEQ ID NO: 1. This is the preferred triple mutant STM sequence.

In another aspect the invention relates to a polypeptide comprising the amino acid sequence shown as SEQ ID NO:3 and the sequence shown as SEQ ID NO:4. These are the preferred STM sequences each side of the preferred Leu73 insertion site.

In another aspect the invention relates to a polypeptide comprising the amino acid sequence shown as SEQ ID NO: 1, or the amino acid sequence shown as SEQ ID NO: 2, wherein a heterologous peptide is inserted at the Leu73 site. Preferably the heterologous peptide inserted at the Leu73 site deletes the Leu73 amino acid residue.

Preferably the heterologous peptide comprises 36 amino acids or fewer, preferably 20 amino acids or fewer, preferably 12 or fewer.

In another aspect the invention relates to an isolated nucleic acid comprising nucleotide sequence encoding the amino acid sequence of SEQ ID NO:1, SEQ ID NO:3 or SEQ ID NO:4.

In another aspect the invention relates to an isolated nucleic acid comprising nucleotide sequence encoding the amino acid sequence of SEQ ID NO:1, wherein the nucleotide sequence comprises a RsrII restriction site. Preferably this RsrII site is at the location in the coding sequence which encodes GP at amino acid residues 72-73.

In another aspect the invention relates to an isolated nucleic acid comprising nucleotide sequence encoding the amino acid sequence of a scaffold protein or polypeptide as described above.

In another aspect the invention relates to a method for identifying a target peptide capable of binding a structure of interest comprising providing a stefin A scaffold protein comprising a target peptide; contacting said scaffold protein with said structure of interest; and monitoring the association between the scaffold and the structure of interest, wherein association of the scaffold protein with the structure of interest identifies the target peptide as a candidate target peptide capable of binding said structure.

In another aspect the invention relates to a polypeptide comprising the amino acid sequence RLNKPLPSLPV ('Peptide A') (SEQ ID NO: 30). Preferably the polypeptide consists of the amino acid sequence RLNKPLPSLPV (SEQ ID NO: 30). In another aspect the invention relates to use of a peptide comprising the amino acid sequence RLNKPLPSLPV (SEQ ID NO: 30) in the manufacture of a medicament for prevention or treatment of yeast infection. Such a peptide is referred to as 'peptide A' herein. Preferably peptide A consists of the amino acid sequence RLNKPLPSLPV (SEQ ID NO: 30). Peptide A is useful in the development of treatments of yeast infections. Peptide A is believed to work by preventing the yeast from being resistant to high osmotic pressure. Thus in another aspect the invention relates to use of peptide A in medicine. Thus in another aspect the invention relates to use of peptide A in the manufacture of a medicament for the prevention or treatment of yeast infection. In another aspect the invention relates to use of peptide A in treating yeast infection. In another aspect the invention relates to a method of treating a yeast infection comprising administering to a subject an effective amount of peptide A. Preferably the yeast infection is a *Candida albicans* infection.

DETAILED DESCRIPTION OF THE INVENTION

Scaffold

As is well known in the art, the term 'scaffold' refers to a protein which can present target peptides to solvent without its own structure being deformed by the target peptide.

Regarding the presentation of peptide to solvent, this can be tested using immunoprecipitation experiments. For example, an indication that a peptide is being presented to solvent may be obtained by its availability to an antibody capable of recognising it. Thus, in order to test the ability of a scaffold protein to present a peptide to solvent, the scaffold comprising the peptide would be expressed and an antibody recognising the peptide would be used to try to immunoprecipitate the scaffold-peptide fusion. If this protein can be immunoprecipitated or captured on the antibody, this shows that the peptide was presented to solvent as is required by a scaffold protein. Another, or an alternative, indication that a peptide is being presented to solvent may be obtained by phosphorylation studies. By incorporating a phosphate acceptor site into the target peptide, and then contacting the scaffold-peptide fusion with the cognate kinase in conditions permissive of phosphorylation, then the presentation of the peptide to solvent can be verified. Phosphorylation of the peptide indicates correct presentation to solvent.

Concerning a scaffold protein's resistance to being deformed by the target peptide which it bears, this can be tested using techniques such as circular dichroism or thermal stability. Specifically, a circular dichroism analysis of a scaffold protein without target peptide inserted into it should be substantially the same as the circular dichroism characteristics of the same scaffold protein when bearing a target peptide. This provides a demonstration that the presence of the target peptide in the scaffold protein has not compromised or deformed the structure of the scaffold protein bearing it. Another way to test this resistance to deformation by the target peptide is by studying the thermal stability of the scaffold protein with and without target peptide inserted. For example, the STM scaffold protein of the present invention can be heated to 98° C. yet will regain its original conformation upon cooling back to room temperature. This property is unaffected by insertion of target peptide up to 20 amino acids in length. With regard to thermal stability, the thermal transition point for STM is approximately 78° C. compared to that of SteA which is 90.8° C. With a peptide inserted, the thermal transition point of STM is 75° C. This is another demonstration that a scaffold protein's structure is not deformed by insertion of the peptide.

A scaffold protein must be able to accept a peptide insert. Preferably the peptide insert is 36 amino acids or less, preferably 20 amino acids or less. Preferably the target peptide insert is 12 amino acids or less.

A scaffold protein must be of known structure. By 'known structure' it is meant that the crystal structure or a solution structure (NMR structure) must be known.

Preferred Features of Scaffold Proteins According to the Present Invention

Preferably a scaffold protein constrains the target peptide. The presence of a constraint effect in a scaffold protein can be demonstrated by comparing the affinity of an entity binding the target peptide when the target peptide is in the scaffold protein with the affinity when the peptide is not in the scaffold protein. A difference in these two affinities indicates that the scaffold protein is constraining the peptide to assume a particular three dimensional conformation. Preferably a scaffold protein constrains a peptide so that it demonstrates an increased binding affinity when present in the context of the scaffold protein. In other words, preferably the scaffold protein decreases the entropic cost of binding and so increases the measured affinity when compared with binding of a free peptide.

In some embodiments, constraint may be provided by a single N-terminal or C-terminal fusion to the target peptide. For example, a peptide may be constrained by fusion to STM 1-73, or by fusion to the C-terminal part of STM. Notwithstanding single N- or C-terminal scaffold fusion embodiments, the meaning of 'constraint' is not altered and whether or not the target peptide is constrained should be judged as discussed herein. Preferably target peptides are inserted into scaffold proteins of the present invention such that scaffold protein sequence is present both N terminally and C terminally to the target peptide.

Preferably a scaffold protein provides the target peptide with an increased stability in vivo. This effect may be demonstrated by comparison of expression of the target peptide in the context of the scaffold protein with expression of the target peptide on its own. Preferably, the target peptide shows increased stability in the context of the scaffold protein.

A scaffold protein is preferably biologically neutral. By 'biologically neutral' it is meant that interactions with other known proteins have been abolished. Furthermore, any signalling abilities possessed by the protein are preferably removed. Thus, a preferred scaffold protein according to the present invention is the STM scaffold protein.

Biological neutrality is an advantage of the present invention since it does not exist in the prior art scaffold proteins. For example, Thioredoxin A acts as a dominant negative of the natural redox pathways in cells. Furthermore, it is known to inhibit P53 and is known to inhibit BCL6 signalling pathways. Advantageously, the scaffold proteins of the present invention do not interfere with naturally occurring signalling pathways.

A scaffold protein should be small. By 'small' is meant less than 25 kDa, preferably less than 13 kDa. Most preferably a scaffold protein should be less than 100aa (excluding target peptide insert).

Preferably a scaffold protein according to the present invention will be conformationally stable. By 'conformationally stable' it is meant that no conformational changes should take place. Preferably a scaffold protein has no hinge region. Preferably a scaffold protein has no PH domain. Preferably a scaffold protein has no SH3 domain. Preferably a scaffold protein has no SH2 domain. Preferably a scaffold protein has no 'WW' domain. Preferably a scaffold protein has no 'WD' domain. Preferably a scaffold protein has no HEAT repeats. Preferably a scaffold protein has no proline rich domain. Preferably a scaffold protein has no post-translational modification in cells. Preferably a scaffold protein has no other domain known to facilitate conformational changes.

A scaffold protein according to the present invention preferably has no protein-protein interaction domains. A protein will be considered to have no protein-protein interaction domains if these have been mutated so as to render them non-functional.

Preferably a scaffold protein according to the present invention has no post translational modifications. Thus, preferably a scaffold protein according to the present invention has no glycosylation site. This is an advantage over prior art scaffold proteins such as dystrophin because post translational modifications can interfere with interactions or create spurious interactions themselves.

As noted above, scaffold proteins should not be deformed by the peptide insert. On this criterion, green fluorescent protein would not be considered a scaffold protein because at least one third of inserted target peptides abolish the fluorescence of green fluorescent protein. This is a demonstration that the target peptide insert is deforming the structure of the protein. Therefore, it is not a scaffold protein according to the present invention since a scaffold protein should preferably not be deformed by the target peptide insert.

Thioredoxin A (TrxA) is a prior art scaffold protein. TrxA is small and is stable. However, the insertion of target peptides into TrxA takes place between two cysteine residues. Scaffold proteins according to the present invention advantageously avoid this arrangement because the cysteine residues in TrxA can undergo reversible disulphide bonding which can alter the conformation of the scaffold protein and can affect the conformation of the presented target peptide. Thus, preferably the insertion site for target peptide is not between two cysteine residues on the scaffold protein.

Design Considerations

Scaffold proteins preferably have one or more of the following features:

1) the scaffold should be of known structure, allowing an informed choice of the site for peptide insertion or replacement;

2) the scaffold should be stable enough to constrain the folding of a broad range of peptides;

3) the scaffold should be flexible enough that its folding not be affected by the insertion of a variety of peptides;

4) the scaffold should be biologically neutral, i.e. lack interactions with cellular proteins that could contribute a phenotype; and 5) the scaffold should be able to fold similarly, preferably identically in both prokaryotic and eukaryotic environments, so that data obtained in one system can inform experiments performed in the other. The invention provides a scaffold suited to the requirements of peptide aptamer technology. The STM scaffold preferably possesses all five of the criteria defined above: the structure of parental Stefin A is known; the engineered scaffold is stable and tolerates the insertion of at least one peptide without losing its biophysical stability; it is able to present a broad range of peptides for functional interaction; and not only have all known biological interactions been engineered away, but we have also abolished interactions between STM and unknown cytoplasmic proteins that apparently anchor parental SteA in the cytoplasm of cells. Finally and crucially, the STM scaffold is well-expressed and able to present biologically active peptides in a range of systems, from in vitro transcription/translation to bacterial, yeast and mammalian cells. In the examples section the AU1 tag target peptide is used to illustrate the invention for peptide aptamers generally. The successful performance of STM in three independent settings (yeast two hybrid, interaction with a protein kinase and interaction with the nuclear import machinery in human cells) indicates that STM is able to present a wide range of peptide sequences for functional interaction.

Further Applications

It will be appreciated by the skilled reader that the use of peptide aptamers in microarrays is particularly advantageous when those peptide aptamers are presented in the scaffold protein according to the present invention. Prior art microarray technology relies heavily on antibodies. However, antibodies can lose specificity when they are bound to the array. Furthermore, recombinant proteins used in microarrays can provide information that proteins are present, but cannot provide information about what is binding them. By contrast, using peptide aptamers displayed in scaffold proteins according to the present invention can advantageously provide a lot more information when an array is interrogated. For example, upon observation of a binding partner, contextual information is advantageously derived when using a scaffold protein to display the aptamer. This advantage is characterised as the difference between a naïve and an informed library. Thus, in another aspect the invention relates to the use of scaffold proteins to display peptides on microarrays.

Preferably the scaffold protein is based on Stefin A. More preferably the scaffold protein comprises STM.

Preferably the scaffold protein according to the present invention is based on the sequence of Stefin A. By 'based on the sequence of Stefin A' it is meant that the scaffold protein should possess at least 70% of the amino acid sequence of Stefin A, preferably 80%, preferably 85%, preferably 90%, preferably 95% or even more of the sequence of Stefin A. Most preferably the scaffold protein will have the sequence of Stefin A and will comprise one or more of the G4W, V48D, and Leu 73 mutations.

The ability of peptide aptamers to disrupt protein-protein interactions in vivo may allow the rapid identification of novel drug leads. Furthermore, the use of small, candidate drug molecule(s) to disrupt protein-protein interaction is advantageously facilitated by the present invention.

Use of peptide inserts comprising post-translational modification sites such as phosphorylation site(s) may be advantageously employed. This is beneficial in dissecting interactions which are varied according to the phosphorylation state of the target peptide. Furthermore, it allows the identification of candidate peptide aptamers which bind in a phosphorylation dependent manner.

In some embodiments, it may be desired to introduce disulphide bonds either side of the target peptide insert, for example by engineering a cysteine residue each side of the target peptide insert. This may be useful if the scaffold is being used exclusively in one setting. In this regard, it is to be noted that the family II cystatins use a di-sulphide bond to form elements of secondary structure that correspond to the preferred region of insertion in STM, showing that STM may also be used to present covalently stabilised peptides if required. In the context of the present invention this can be achieved for example by the addition of a single cysteine at the C-terminus of the scaffold polypeptide, or within the target peptide such as at the C-terminal end of the target peptide, and addition of a second cysteine residue inserted at a second location such as in the N-terminus of the scaffold or at the N-terminal end of the target peptide, thus allowing cross-linking between the two. However, it is preferred to avoid the covalent constraint of peptides in this manner. Thus, in preferred scaffolds of the present invention, preferably the target peptide is not flanked by cysteine residues.

Overall it will be appreciated that different scaffolds may force a bias on the peptides they present, so that study of target peptides may advantageously involve peptides and/or libraries presented in more than one scaffold, so as to maximise the likelihood of success.

Scaffolds of the invention such as STM allow investigators to extend in vitro observations to the intracellular environment and vice versa, as well as allowing the in vitro identification or creation of tools that may be used inside cells without concerns about folding patterns or the oxidation state of disulphide bonds.

The ease of expression of STM and STM based peptide aptamers in recombinant form and the longevity of the proteins at 4° C. indicate that STM based peptide aptamers are suitable for protein microarray applications. We also note that the thermostability of STM allows easy purification of STM based peptide aptamers from heat-treated *E. coli* lysates.

Peptide aptamers based on scaffolds of the present invention such as STM are tools that can be used to validate drug targets, that can be used as components of diagnostic or prognostic tests or even form the basis for lead compounds for the treatment of human disease. The scaffolds of the invention, advantageously based on a full-length human protein, may be useful as biological therapeutics and/or in gene therapy.

Target Peptide

The term 'target peptide' as used herein refers to a peptide of interest. The target peptide is preferably a heterologous peptide. By heterologous is meant a peptide which is removed from its usual context, preferably a peptide having a sequence not usually found in the sequence of the scaffold protein bearing, carrying or displaying it. If the peptide does have a sequence which occurs elsewhere in the sequence of the scaffold protein, then for it to be 'heterologous' that sequence will be out of context ie. not occupying its naturally occurring position (address) within the scaffold protein polypeptide. In this context, 'position' and means position within the linear amino acid chain rather than position in three dimensional space relative to other amino acid residues. The target peptide may be artificial for example generated by the construction of a library of peptides for incorporation into the scaffold protein. In these embodiments, the artificial peptide(s) are considered to be 'heterologous' for the purposes of the invention.

Peptide Aptamers

Peptide aptamers are peptides constrained and presented by a scaffold protein that are used to study protein function in cells. Some are able to disrupt protein-protein interactions and some are able to constitute recognition modules that allow the creation of a molecular toolkit for the intracellular analysis of protein function.

The ability to design or identify small molecules that can bind specifically and with high affinity to a given protein is a rate-limiting step in many experiments, including the development of protein microarrays, the analysis of proteins in the context of living cells and the validation of candidate drug targets. In nature, protein-protein interactions can be mediated by small surfaces of folded proteins. This has led to the use of small peptide surfaces presented within the context of a stable protein, called the scaffold, as protein recognition modules. Such reagents, called here peptide aptamers, have been used to disrupt biological protein activity in a range of systems.

Peptide aptamers are more easily delivered and more stable in cells than free peptides and their constrained folding results in a lower entropic cost of binding and hence increased affinity for target proteins. Protein engineering of peptide aptamers allows them to provide the recognition functionality in the design of a molecular toolkit although this potential has yet to be fully realized. The affinity of peptide aptamers for their targets ranges from $10^{-6}$ to $5 \times 10^{-9}$ M compared to $K_d$ $10^{-7}$ to $10^{-11}$ M for antibody/target interactions. Nonetheless, peptide aptamers are clearly able to disrupt protein-protein interactions in vivo. Peptide aptamer screens are performed in yeast or in mammalian cells, which distinguishes them from phage display screens of peptide or antibody libraries performed against potentially misfolded prokaryotically expressed protein.

While the most extensively used scaffold is the *Escherichia coli* protein thioredoxin (TrxA), a number of other proteins have been used. The success of this technology hinges upon the robustness of the scaffold, yet one third of peptides may destabilize GFP, while many TrxA based peptide aptamers are not stably expressed in cultured human cells, suggesting that this scaffold also may not be rigid enough to present peptides without becoming itself partially unfolded. Peptides taken out of the context of one scaffold and placed in another frequently lose the ability to interact with their target proteins, raising the possibility that screens for constrained interactors with a given target may fail unless an appropriate scaffold is used. Finally, the biological activities of scaffolds used to present peptides have not been rigorously characterized in the prior art, leading to concerns that any phenotype observed when a peptide aptamer is expressed could, at least in part, be due to an effect of the scaffold and not the inserted peptide.

We have therefore produced a robust, versatile, biologically neutral scaffold for the presentation of constrained peptides. We sought a protein that could be stably expressed in a range of experimental systems while presenting peptides that are able to interact functionally with a wide range of targets. Such a scaffold substantially improves peptide aptamer technology by increasing its robustness. In addition, by expanding the repertoire of available scaffolds, the present invention advantageously increases the likelihood that hits will be obtained in screens against a greater number of target proteins by using libraries in multiple scaffolds in simultaneous screens against each target.

Stefin A

Here, we describe the development of a rigorously tested and biologically inert scaffold for the presentation of constrained peptides, based on human Stefin A (SteA). SteA is the founder member of the cystatin family of protein inhibitors of cysteine cathepsins, which are lysosomal peptidases of the papain family. The stefin sub-group of the cystatin family are relatively small (around 100 amino acids) single domain proteins. They receive no known post-translational modification, and lack disulphide bonds, suggesting that they will be able to fold identically in a wide range of extra- and intracellular environments. SteA itself is a monomeric, single chain, single domain protein of 98 amino acids. The structure of SteA has been solved (Martin et al. 1995 *J Mol Biol*. vol 246 pp 331-43; Tate et al 1995 *Biochemistry* vol 34 pp 14637-48; Jenko et al 2003 *J Mol Biol*. vol 326 pp 875-85), facilitating the rational mutation of SteA into the STM scaffold. The only known biological activity of cystatins is the inhibition of cathepsin activity, which allowed us to exhaustively test for residual biological activity of our engineered proteins. Thus, we disclose that protein engineering of native SteA can produce variants that are useful as peptide aptamer scaffolds. We show that SteA can be engineered to lose its biological activity in vitro and in the cellular context, creating in a preferred embodiment an artificial protein we call STM (Stefin A Triple Mutant). Biophysical methods show that the STM scaffold with a peptide inserted retains the folding and thermostability of the parent protein. We show that STM is able to access both the cytoplasm and the nucleus of human cells, making it a versatile tool for the exploration of the biology of human proteins. The engineered scaffold readily presents peptides for interaction both in vitro and in bacterial, yeast and mammalian cells. Finally, we show that STM is able to present a range of designed peptides that can interact successfully with a known target. The peptide aptamer prior art has been hampered by difficulties in identifying biological activity in cell-based assays, caused at least in part by sub-optimal performance of the various existing scaffolds. We have created a useful scaffold that will be of great benefit to those seeking to study protein-protein interactions in vitro and in vivo.

Stefin A Sequences

A scaffold 'based on' stefin A has a sequence which is derived from stefin A. Preferably the sequence derived from stefin A comprises the stefin A wild type sequence, preferably comprising one or more of the modifications (mutations) described herein, preferably comprising the STM sequence, preferably comprising the STM sequence bearing a target peptide inserted at the Leu73 site.

It will be apparent to a person skilled in the art that minor modifications may be made to the scaffold sequence without departing from the invention. In particular, the invention relates to amino acid sequences and/or nucleotide sequences which have at least 60% identity to the corresponding sequences shown herein, preferably at least 70%, preferably at least 80%, preferably at least 85%, preferably at least 90%, preferably at least 92%, preferably at least 94%, preferably at least 95%, preferably at least 96%, preferably at least 97%, preferably at least 98%, preferably at least 99% identity, or even more. In each case, sequence variations are considered 'minor' if they do not adversely affect the ability of the scaffold to present the target peptide to solvent, and do not restore or generate biological functions such as those which are possessed by wild type stefin A but which are abolished in the G4W, Leu73 or V48D mutants, and preferably do not restore any biological function abolished by the STM triple mutant.

Furthermore, minor modifications may also include small deletions or additions to the stefin A or stefin A derived sequences disclosed herein, such as addition or deletion of 10 amino acids or fewer to the stefin A derived polypeptide. Thus the invention relates to amino acid sequences having a total addition or deletion with respect to the stefin A or STM sequences disclosed herein of 40 amino acids or fewer, preferably 30 amino acids or fewer, preferably 20 amino acids or fewer, preferably 15 amino acids or fewer, more preferably 10 amino acids or fewer, preferably 9 amino acids or fewer, preferably 8 amino acids or fewer, preferably 7 amino acids or fewer, preferably 6 amino acids or fewer, preferably 5 amino acids or fewer, preferably 4 amino acids or fewer, preferably 3 amino acids or fewer, preferably 2 amino acids or fewer, preferably 1 amino acid. The total addition or deletion is the important factor, so that a difference of 9 or fewer may mean a deletion of 9 amino acids, or three deletions each of three amino acids, two additions of three amino acids and one deletion of three amino acids and so on. The invention also relates to the corresponding nucleic acid variants. In each case, sequence variations are considered 'minor' modifications if they do not adversely affect the ability of the scaffold to present the target peptide to solvent, and do not restore or generate biological functions such as those which are possessed by wild type stefin A but which are abolished in the G4W, Leu73 or V48D mutants, preferably do not restore any biological function abolished by the STM triple mutant.

Stefin A Mutations

Preferred stefin A mutations are discussed in turn below.

In the context of discussing mutation sites, 'close to' means within 7 amino acids, preferably within 5 amino acids, preferably within 3 amino acids, preferably within 2 amino acids, preferably at the nominated amino acid or one of the two neighbouring amino acids.

In the context of insertions, it is preferred that at the nucleic acid level restriction site(s), preferably unique restriction site(s), are introduced to facilitate future insertions. This is discussed in some detail in connection with the Leu73 site. These teachings and common general knowledge in the art of recombinant nucleic acid technology enable the skilled worker to introduce the relevant restriction site(s) whilst preserving the key features of the scaffold. By 'unique' is meant unique in the coding sequence of the scaffold protein. Non-unique sites may be used, but unique sites are preferred for ease of insertion and manipulation of the constructs. Where two or more sites are used for example to facilitate removal and replacement of the sequence encoding the Leu73-80 loop of SteA, preferably each of the two or more sites is unique. However, if the two or more sites are identical it may advantageously simplify the removal and replacement operations, for example by involving only a single restriction enzyme treatment. These choices are well within the ability of the skilled person working the invention. In a preferred embodiment, two identical sites are introduced for removal and replacement of the Leu73-80 loop. Preferably restriction sites used at the sequences coding for the Leu73, G4 and V48 regions are different so that insertions or modifications at each of these three locations in the coding sequence can be made using a different restriction enzyme for ease of manipulation.

G4W Mutation

The term 'G4W mutation' is used herein to describe mutation around, preferably close to or preferably at, the G4 site of stefin A, or stefin A derived polypeptides. In a broad embodiment, G4W mutation refers to addition(s) or insertion(s) or replacement(s) to the amino terminus amino acid residue(s) of SteA. Preferably such mutations are proximal to Pro14, preferably proximal to G4. Preferably such mutations are close to, or preferably at, the Pro14 of human SteA. Preferably such mutations are close to, or preferably at, the G4 residue of human SteA. Particularly preferred G4W mutation is as demonstrated by the STM sequence. Most preferred is replacement of G4 with W.

In a preferred embodiment, the G4W site is used as a secondary insertion site in addition to the Leu73 site, or even as a tertiary insertion site in addition to both the Leu73 and V48D sites.

V48D Mutation

The term 'V48D mutation' is used herein to describe mutation around, preferably close to or preferably at, the VAG site of SteA. The VAG site is residues 48-50 of the QVVAG site (SEQ ID NO: 88) which is at residues 46-50 of human SteA.

Preferably this refers to addition(s) or insertion(s) or replacement(s) around, preferably close to or preferably at the VAG site residues 48, 49, 50 of human SteA. Preferably this refers to additions to or insertions into the VAG site (residues 48, 49, 50 of human stefin A), preferably close to or most preferably at the V residue of this sequence. Particularly preferred V48D mutation is as demonstrated by the STM sequence. Most preferred is replacement of V48 with D.

In a preferred embodiment, the V48D site is used as a secondary insertion site in addition to the Leu73 site.

Leu 73 Mutation

The Leu 73 site represents the preferred insertion site for target peptides according to the present invention. This was chosen because it represents a solvent exposed loop of the Stefin A protein, and is therefore amenable to the display of target peptides in a solvent accessible manner. Preferably this property is preserved by mutations at this site.

The term 'Leu73 mutation' is used herein to describe mutation around or preferably close to or preferably at the L73-L80 loop of human SteA.

The term may refer to addition(s) to or insertion(s) at, or replacement of, leu80 of human stefin A. Preferably the term refers to addition(s) or insertion(s) at, or replacement of, leu73 of human stefin A.

In one embodiment, the Leu73 mutation may comprise replacement of the whole loop between L73 and L80 with any peptide sequence, preferably with a range of different target peptide sequences (preferably only one per stefin scaffold molecule) ie. a library.

At a nucleic acid level, preferred mutations are those which result in a restriction site for insertion in the leu73-leu80 loop, and more preferably two restriction sites for replacement of the sequence encoding this loop. Particularly preferred are restriction sites which are unique to the stefin A scaffold coding sequence. Most preferred is the RsrII restriction site.

In a highly preferred embodiment the Leu73 mutation corresponds to that shown in the STM protein, and preferably the corresponding RsrII nucleic acid sequence is present in the nucleic acid encoding same. Thus in a preferred embodiment the KSL amino acid sequence of SteA at residues 71-73 (ie. Leu73) is replaced by a NGP amino acid sequence at the same address (residues 71-73) as in the STM sequence. The STM sequence is preferably not expanded relative to the SteA sequence but preferably remains at 98 amino acids.

It will be noted that in these embodiments, that insertion of the peptide using the RsrII site leads to an extra two amino acids being introduced (ie. the nucleotide sequence of the RsrII site codes for GP). This is because following ligation the RsrII site will be duplicated. References to a 'unique' RsrII site herein refer to nucleic acid encoding the scaffold without the peptide insert. Thus, for the avoidance of doubt, references to the length of the peptide insert refer to the heterologous amino acid sequence of interest and do not include the extra two amino acids (GP) introduced by the RsrII site. Thus, introduction of a 20mer peptide leads to a scaffold-peptide fusion of 120aa (98aa (scaffold)+20aa (target peptide)+2aa (GP)=120aa). Preferably the target peptide is introduced at this site thus: *NGPX-XGP** (SEQ ID NO: 89), wherein '*' and '**'=remainder of the scaffold sequences, and 'X-X'=target peptide. Preferably X-X comprises 20 or fewer amino acids, preferably 12 or fewer amino acids.

Combination Mutations

Preferably a scaffold protein according to the present invention is based on Stefin A and comprises at least one of the mutations described above. Preferably the scaffold protein comprises the Leu 73 mutation. Preferably the scaffold protein comprises the target peptide inserted at the Leu 73 site.

Preferably the scaffold protein comprises at least two mutations as described above. When a scaffold protein of the present invention comprises only two mutations, preferably these are not just the G4W and Leu 73 mutations. When the scaffold protein of the present invention comprises only two mutations, preferably these mutations are the V48D and Leu 73 mutations.

Preferably a scaffold protein according to the present invention possesses all three mutations described above. Therefore, preferably a scaffold protein according to the present invention has the G4W, V48D, and Leu 73 mutations in combination.

Concerning the G4W mutation, this is particularly advantageous for use in enhancing avidity and/or specificity of entities binding the target peptide inserted at the Leu 73 site and/or the V48 site on the scaffold protein.

Concerning the V48D mutation, this represents another solvent exposed loop in the Stefin A structure. This is particularly advantageous for use in enhancing avidity and/or specificity of entities binding the target peptide inserted at the Leu73 site and/or at the G4W site on the scaffold protein. Thus, the invention embraces the use of V48D as a secondary or tertiary insertion site in a scaffold protein based on Stefin A.

Target peptides may advantageously be inserted at any of the three preferred mutation sites G4W and/or V48D and/or Leu73. Preferably they are inserted at V48D and/or Leu73. Preferably they are inserted at Leu73.

In the highly preferred embodiment, Stefin A based scaffold proteins allow the use of three surfaces in total. These are the surfaces defined by the Leu 73 loop, the V48D loop, and the G4W loop. These loops are shown in three dimensional form in FIG. 1*b*. Most prior art scaffold proteins use only a single surface, and therefore it is an advantage of the present invention that multiple surfaces can be used on a single scaffold protein. One prior art protein which allows multiple surfaces to be used is composed of repeats of the dystrophin domain. However, this cannot be used in the mammalian cells since it is a mammalian structural protein which has so many relatives and partner proteins that it is unlikely to be biologically neutral.

Solid Phase and Microarrays As noted above, the invention finds application in microarrays. In solid phase embodiments such as microarray embodiments, the scaffold protein is preferably engineered to facilitate its association or attachment to the solid phase substrate for the assay. Preferably this is by sticking to a gold coating, or by association with biotin. In order to engineer the scaffold for sticking to gold coating, preferably one or more Cys residues is introduced at the C or N terminus of the scaffold protein. In order to engineer the scaffold for immobilisation by attachment to biotin, preferably an eight amino acid biotin binding domain ('streptag') is introduced into said scaffold. Immobilisation may be by one or more of these or any other suitable means. Preferably the scaffold protein of the invention is immobilised. Preferably the scaffold protein of the invention is engineered for immobilisation. Preferably interaction tests according to the present invention are carried out using immobilised scaffold protein.

Further Advantages of the Invention

Scaffold proteins based on Stefin A are superior to using peptides because they can be used in vivo. Furthermore, employing recombinant systems they are cheaper than working with synthetic peptides. Furthermore, construction of libraries is cheaper than using synthetic libraries for the same reason, and also because they can be rationally designed using nucleic acid manipulation. This reduces the reliance on complicated chemistry for peptide synthesis.

Scaffold proteins based on Stefin A are superior to prior art such as phage display since they are internal to the cell, whereas phage display relies on extracellular interaction. Furthermore, scaffold proteins of the present invention can be used to work on native targets rather than recombinant targets. This has a further advantage of allowing examination of post translationally modified proteins which will be correctly phosphorylated or glycosylated or otherwise post-translationally modified in vivo but which would probably not be correctly formed if produced in vitro.

A further advantage of scaffold proteins according to the present invention is that they allow interrogation of the naturally occurring spectrum of splice variants and post translational modification variants which are produced in vivo without having to individually manufacture each of them and array them or otherwise compartmentalise them for analysis.

A further application of the invention is in the use of microcantilevers as a read out for interaction with Stefin A based scaffold proteins. Furthermore, the scaffold proteins of the present invention are particularly suitable for use with thin film transistor type readouts.

The present invention will now be described by way of example, in which reference will be made to the following figures.

BRIEF DESCRIPTION OF THE FIGURES

FIG. 2. Shows blots which demonstrate that recombinant STM retains characteristics of the wild type protein, and can present peptides to solvent. Panel A: Wild type Stefin A, the STM variant, and STM with a 6 amino acid peptide (DTYRYI) (SEQ ID NO: 32) inserted remain soluble after a 20 minute incubation at 75° C. In addition, the domain swapped dimer form of wild-type SteA whose formation is promoted by heat-treatment is absent from the STM forms. Panel B: STM carrying the AU1 epitope tag can be quantitatively and specifically depleted from E. coli lysates with an anti-AU1 antibody.

FIG. 3. Shows graphs which illustrate the biochemical and biophysical characterisation of STM. This shows that the folding of STM closely parallels that of SteA. Panel A. Gel filtration chromatography of recombinant STM (solid lines) and SteA (dashed lines) with (red) and without (blue) prior heat treatment were flowed over a gel filtration column. Wild type SteA elutes in two peaks, indicating the monomeric and heat-promoted dimeric domain-swapped forms, whereas STM elutes as a monomer even after heat treatment. Panel B: Circular dichroism indicates the highly structured nature of SteA, and in particular the high proportion of SteA that is composed of beta sheet. Panel C: the folding elements of STM detected by CD are identical to those of wild type SteA, indicating that the two variant proteins fold in substantially similar, or even identical, ways.

FIG. 7 shows a diagram (7A), a photograph of cell patches (7B), a photograph of a blot (7C) and photographs of three blots (7D).

FIG. 8a discloses SEQ ID NOS 86-87, respectively, in order of appearance.

FIG. 9 shows Identification of a peptide aptamer that causes osmo-sensitivity

A. Peptide aptamers that interact with the Sho1 SH3 domain were expressed under the control of the Gal1 promoter in the yeast strain TMY182 (W303 Δssk2/Δssk22 background), where osmo-resistance depends upon the integrity of the Sho1 arm of the HOG pathway, in the presence of 1M NaCl. When the expression of peptide aptamers is induced by galactose in the medium, yeast cells expressing AptA were osmotically sensitive whereas those expressing other peptide aptamers were viable.

B. Western blot of yeast lysate with an antibody that recognises phosphorylated, active Hog1 confirms that AptA results in osmotic lethality by inhibiting Hog1 activation.

Figure 10:
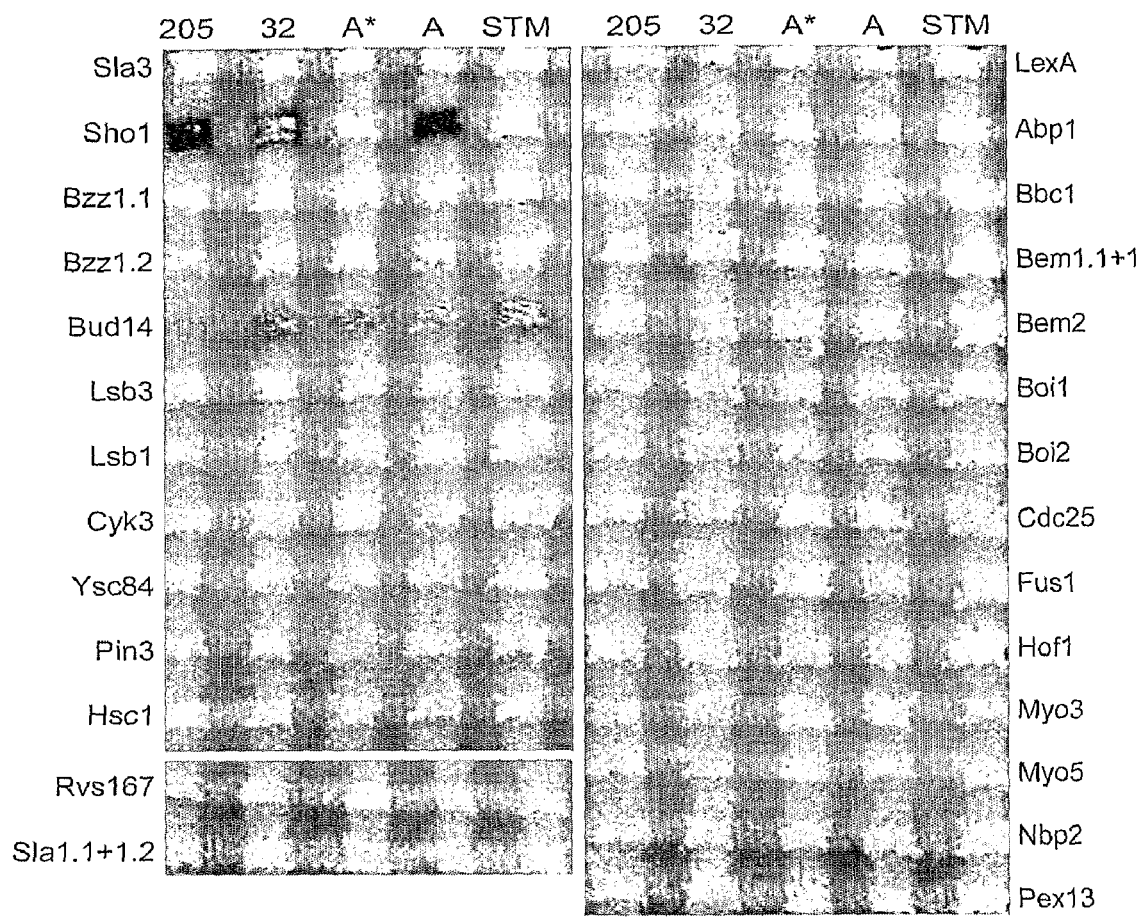

FIG. 10 shows Proteome-wide specificity array of 28 yeast SH3 domains.

The yeast genome encodes 25 proteins that between them comprise 28 SH3 domains. Each domain, or combination of domains, was cloned as a yeast two hybrid bait, and tested by interaction mating for its ability to recognise AptA. Replacement of the two prolines in the PxxP motif of AptA with alanine residues to create AptA* abolished binding to Sho1 SH3, indicating that AptA is a bona fide SH3 ligand. The SH3 domain of Bud14 is a self-activating bait, giving rise to a blue colour even when mated to an empty prey plasmid. 05 and 32 are two peptide aptamers that were isolated from the screen but do not inhibit signaling. AptA* is the mutant version of AptA where the two proline residues of the PxxP motif have been changed to alanines (PP/AA). STM is the empty scaffold.

FIG. 11 shows Membrane re-tethering of Pbs2 by AptA reconstitutes the signaling pathway.

Panel A: Schematic of the strategy to re-tether SH3 binding-impaired Pbs2 to Sho1 by fusion to AptA. The mutation of prolines 96 and 99 of Pbs2 to alanines abolishes the ability of Pbs2 to bind to Sho1-SH3 [19]. Fusion of AptA to Pbs2 should create a chimeric proteins that has the functions of Pbs2 (interaction with Ste11, Hog1 etc) and the ability to bind to Sho1 once more. In contrast, fusion of the mutant Pbs2 to STM should not create a functional chimera. Panel B. Yeast spot assay showing that the recombinant Pbs2(AA)-Apt functions in a similar manner to wild type Pbs2, and allows signalling. As before, yeast expressing AptA are osmotically sensitive. This experiment indicates that AptA is able to recruit Pbs2 (P96A/P99A) to the Sho1 receptor, and confirms that the osmo-sensitive phenotype of AptA is due to interaction with Sho1.

FIG. 12 shows AptA prevents the normal assembly of the Sho1 signaling complex.

A. Yeast cell lysate was incubated with GST-Sho1 SH3 beads and passed over a glutathione-agarose column. After extensive washing, bead-bound proteins were eluted with reduced glutathione. Western blotting shows a reduced amount of Hog1 associated with the Sho1-SH3 interaction complex in the presence of Apt A, indicating their physical interaction was disturbed by Apt A but not the control peptide aptamer.

B. Model scheme summarising this work and its implications.

Figure 13:
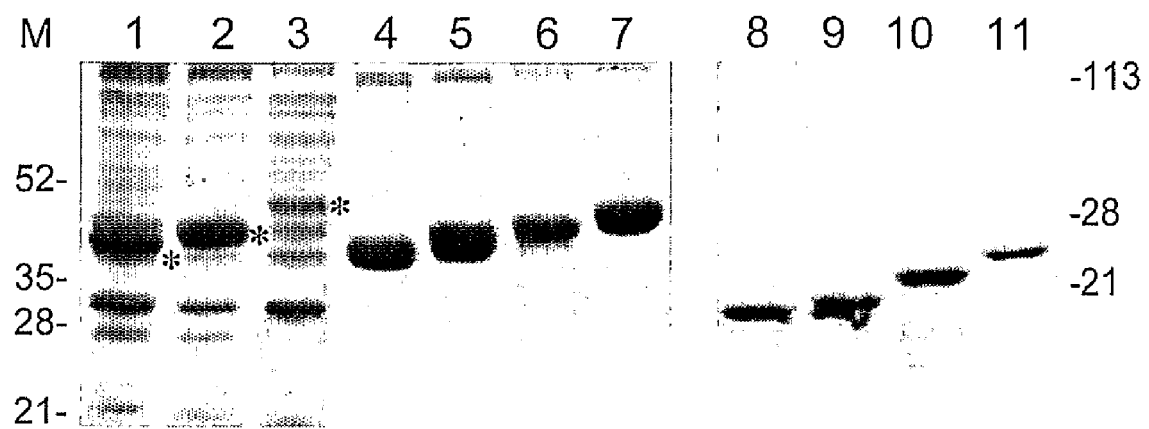

FIG. 13 shows expression and purification of STM peptide aptamers

Recombinant GST-STM or -STM peptide aptamers were expressed in BL21 DES3 pLys cells followed by affinity chromatography on Glutathione beads. Peptide aptamers with inserts of different lengths (Apt05: 12 amino acid residues; Apt206: 26 residues; Apt201: 40 residues) were subjected to SDS-PAGE and are visualised with Coomassie stain. Lanes 1-3: 0.01% input of soluble fraction of the total cell lysate (1: GST-STM, 2: GST-Apt05, 3: GST-Apt 206). Lanes 4-7: Glutathione bead fractions with bound proteins (4: GST-STM, 5: GST-Apt05, 6:GST-Apt206, 7: GST-Apt201). Lanes 8-10: STM peptide aptamers cleaved from GST fusion by PreScission Protease. (8: STM; 9:Apt05; 10: Apt206; 11:Apt201).

Figure 14:
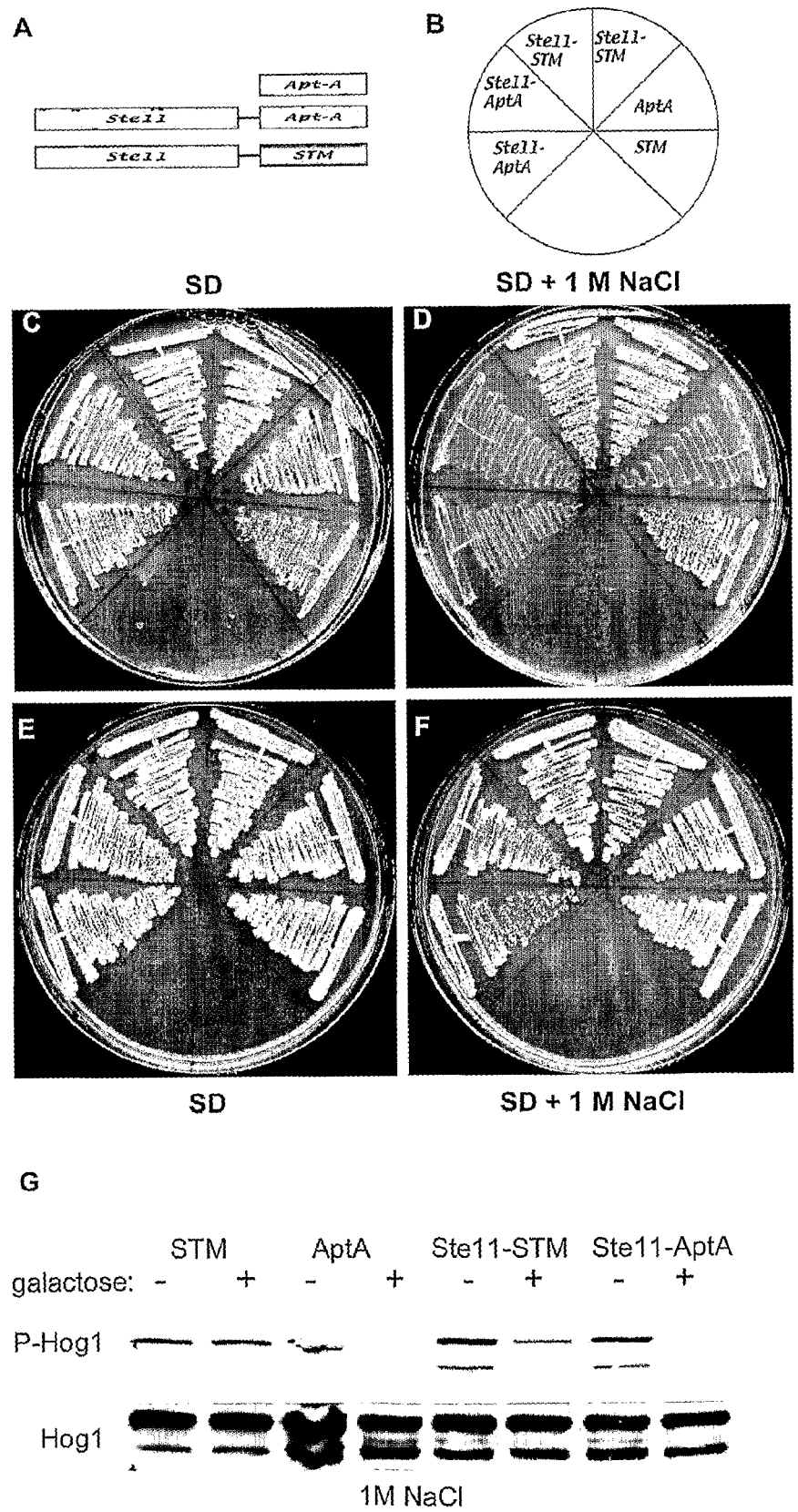

FIG. 14 shows a fusion of AptA to Ste11 does not confer osmo-resistance.

Panel A: The constructs expressed were either STM or AptA alone, or a fusion to Ste11 of STM, which should not interfere with Ste11 function, or of AptA, which should target Ste11 constitutively to Sho1. Panel B: Schematic layout of the plates shown in panels C-F. Panel C: Control plate to show that the galactose-induced expression of AptA, or the AptA-Ste11 fusion, is not in itself toxic to yeast. Panel D: as panel C, except that the medium was supplemented with 1M NaCl to induce the osmotic shock response. In the presence of 1M NaCl, cells expressing either AptA, or a fusion of AptA to Ste11, are unable to grow. Cells expressing either STM, or STM fused to Ste11, are resistant to the osmotic stress. Panels E and F: Control plate containing glucose, that represses the expression of the fusion proteins shown in Panel A, to show that the inability to grow on high salt is dependent on the expression of AptA, or Ste11-AptA. Panel G: Western blot showing that Hog1 MAPK is not phosphorylated when cells express either AptA or the AptA-Ste11 fusion. The inability of Step 11-Apt to restore Hog1 activation indicates that AptA is still functional in this chimera but Ste11 is not.

EXAMPLES

The examples make use of the following techniques and procedures:

Plasmids and DNA Manipulation pcDNA3SteA carries the SteA open-reading frame under the control of the cytomegalovirus promoter (J.P. Waltho, University of Sheffield, UK). pcDNA3.1 HisA and pcDNA3.1 His/Myc B for the construction of hexa-histidine tagged (SEQ ID NO: 124) proteins in mammalian cells were purchased from Invitrogen (Paisley, UK), pGILDA from Origene (Rockville, Md., USA). pET30a(+), for the expression of hexa-histidine tagged (SEQ ID NO: 124) proteins in bacteria was purchased from Novagen (Nottingham, UK) and pGFP²-C2 from Perkin Elmer (Boston, Mass., USA). Yeast two hybrid plasmids (including pEG202, pJG4-5 and pJM-1) and strains are from Molecular Sciences Institute, Berkeley, Calif., USA. pRS306 GFP-Sho1p is from the Dana-Farber Cancer Institute, Boston, Mass., USA. DNA manipulations were performed as described by Sambrook and Russell (2001 'Molecular Cloning, a Laboratory Manual' Cold Spring Harbor Laboratory Press, Cold Spring Harbor, N.Y.), using enzymes obtained from NEB (MA, USA). Oligonucleotides were from Sigma-Genosys (Pampisford, UK) and are given in the sequence listing. Site directed mutagenesis was performed using the Multisite Site Directed Mutagenesis kit (Stratagene, Cedar Creek, Tex., USA). All DNA manipulations were confirmed by sequencing.

Plasmids for Expression in Mammalian Cells

The SteA open reading frame was PCR amplified using primers P1 and P2 (sequence listing) from pcDNA3SteA and cloned between the EcoRI and EcoRV sites of pcDNA3.1 HisA creating SteA pcDNA3.1 HisA. An RsrII site was introduced into this construct by site directed mutagenesis using oligonucleotide P3, creating RS pcDNA3.1 HisA, where codons 71 to 73 of the ORF are altered, changing the protein sequence from KSL to NGP. The RS ORF was PCR amplified using primers P4 and P5 and RS pJG4-5 (see below) as a template, and cloned between EcoRI and XbaI sites of pcDNA3.1 His/Myc B creating RS pcDNA3.1 His/Myc B. The DS open reading frame was PCR amplified from DS pJG4-5 (see below) using primers P6 and P7, changing the coding of codon 4 from glycine to tryptophan. The PCR product was cloned EcoRI-XbaI into pcDNA3.1 His/Myc B to create STM pcDNA3.1 His/Myc B. The DS open reading frame was separately PCR amplified from DS pJG4-5 using primers P8 and P9 that introduced both the third G4W mutation and an N-terminal NLS, the PCR product being cloned EcoRI-XbaI to create NLS STM pcDNA3.1 His/Myc B. STM was subcloned EcoRI-EcoRI from STM pJG4-5 into pGFP$^2$-C2 to create STM pGFP$^2$-C2. This was converted to STM 1×NLS pGFP$^2$-C2 by inserting a dsDNA cassette created by annealing oligonucleotides P10 and P11 encoding the SV40 T NLS (PKKKRKV) (SEQ ID NO: 31) flanked by AvaII restriction sites into the RsrII site of the STM open reading frame. Concatameric ligation of two cassettes into the RsrII site created STM 2×NLS pGFP$^2$-C2.

Plasmids for Expression in *Saccharomyces cerevisiae*

RS was PCR amplified from RS pcDNA3.1 HisA using primers P12 and P13 and cloned EcoRI-EcoRI into pJG4-5 (Gyuris et al, 1993) in frame with the B42 activation domain to create RS pJG4-5. We suggest that the use of the relatively weak transcriptional activation domain in this plasmid will allow the selection of peptide aptamers with a high affinity for their target proteins. Site directed mutagenesis of RS using oligonucleotide P14 introduced the V48D mutation, creating DS pJG4-5. Oligonucleotide P15 altered codon 4 to encode tryptophan, creating STM pJG4-5. STM pJG4-5 was subsequently altered by site directed mutagenesis so that the sequence surrounding the RsrII site matched that of TrxA, using primer P26. All subsequent manipulations described used this altered form of STM. STM was subcloned from STM pJG4-5 into pGILDA using the flanking EcoRI sites to create STM pGILDA. Oligonucleotides encoding the peptide sequences of all 14 CDK2 interactors identified by Colas (1996 *Nature* vol 380 pp 548-50) were cloned into STM pJG4-5 for yeast two hybrid interaction assays. The SH3 domain of Sho1p was PCR amplified from pRS306 GFP-Sho1p using primers P24 and P25. The digested PCR product was cloned into EcoRI/NotI digested pEG202 to make pEG202-Shot-SH3.

Plasmids for Expression in *Escherichia coli*

The SteA ORF was PCR amplified using primers P16 and P17 and SteA pcDNA3.1 HisA as template, and cloned using EcoRI-XhoI into pET30a(+) to create SteA pET30a(+). Site directed mutagenesis with the oligonucleotides described in the previous section was used to create RS pET30a(+) and STM pET30a(+). A double stranded oligonucleotide cassette flanked by AvaII overhangs encoding the AU1 epitope tag DTYRYI (SEQ ID NO: 32) was made by annealing oligonucleotides P18 and P19. The dsDNA AU1 insert was ligated into the RsrII site of STM pET30a(+) to create STM AU1 pET30a(+)

Construction of STM Peptide Aptamers: Preparation of Library DNA

Degenerate single-stranded oligonucleotide P21 for the yeast two hybrid SH3 screen was made double stranded by PCR using P20 to prime the reaction, and the AvaII digested cassettes ligated into the RsrII site of STM pJG4-5 following the methods of Colas (1996 *Nature* vol 380 pp 548-50) and Geyer, C. R. (2000 *Current Protocols in Molecular Biology* F. M. Ausubel et al, Eds. 24.4.1-24.4.25.).

Occasional ligation of oligonucleotides to each other as well as to the vector leads to the expression of multiple peptides in one scaffold. The ligated DNA was used to transform *E. coli* XL10 Gold Cells (Stratagene) from which midiprep DNA was isolated (Qiagen) and transformed into yeast. The quality of libraries was tested by sequencing plasmids isolated from 30 separate clones either before or during subsequent screens.

Preparation of Yeast Libraries

All yeast methods were as described in Rose et al (Eds). (1990 Methods in Yeast Genetics: a Lab course manual. Cold Spring Harbor Laboratory Press, Cold Spring Harbor, N.Y.). Transformation of library DNA into yeast resulted in approximately 5000 colonies per μg. Transformed yeast were recovered and grown in selective media for four hours at 30° C. with shaking (250 rpm). Cells were recovered by centrifugation at 1000×g, washed in ultrapure water and resuspended in 25% glycerol to be frozen in aliquots at −80° C. The number of colony forming units per aliquot was determined by serial dilution of a thawed aliquot on selective plates.

Expression and Detection of Proteins in Yeast

Cells from overnight cultures of single yeast colonies carrying pJG4-5-STM were grown in 10 mL of medium containing the appropriate carbon source (glucose or galactose at 2% v/v) for protein repression or expression respectively. Cells were recovered by centrifugation as before, washed in ultrapure water and resuspended in 1 mL protein extraction buffer (50 mM Tris.Cl pH7.4, 2 mM EDTA, 100 mM NaCl with Complete protease inhibitors [Roche]). Lysis was by vigorous vortexing for 10 minutes at 4° C. with 400/600 micron glass beads (Sigma). The beads and cell debris were pelleted by centrifugation for 1 min at 13,000 rpm in an Eppendorf 5415 microfuge, and 10 μL of the supernatant used for SDS-PAGE and immunoblot analysis.

Production of SteA and SteA Variant Recombinant Proteins in *E. coli* pET30a(+) SteA and SteA variants transformed into *E. coli* BL21 (DE3) cells were grown to $A_{600}$=0.6 in 2×TY broth and protein expression induced with 0.4 mM IPTG for 2 hours. Cells were harvested and resuspended in Bugbuster protein extraction reagent (Novagen) supplemented with 15 mM imidazole. The cells were lysed by sonication using a VibraCell sonicator (Sonics and Materials Inc) at 80V for 3×30 seconds. Six-His tagged (SEQ ID NO: 124) proteins were purified using Ni-NTA columns (Qiagen) and eluted with 500 mM imidazole into TBS 300 (Tris Buffered Saline supplemented with 300 mM NaCl). The proteins were then dialysed into 1×TBS overnight at 4° C.

Thermostability Assay

Recombinant SteA and variants were incubated at 75° C. or on ice for 20 minutes, and denatured protein pelleted by centrifugation for 1 min at 13,000 rpm in an Eppendorf 5415 microfuge. Soluble heat-treated and non-treated proteins were separated by denaturing SDS polyacrylamide gel electrophoresis and visualized by coomassie staining.

STM AU1 Immunoprecipitation

SteA protein preparations were pre-cleared by incubation of 100 ng of recombinant SteA or SteA variant with 20 µl of Sephadex Protein A/G beads (Amersham Pharmacia) in 500 µl 1×TBS with 1 mg/ml BSA for 1 hour at 4° C. The beads were recovered by centrifugation and discarded and the pre-cleared supernatant reserved. For immuno-precipitation, 0.1, 1 or 10 µg of anti-AU1 antibody (Babco) were bound to 20 µl Protein A/G beads (Sigma) in 500 µl 1×TBS with 1 mg/ml BSA for 1 hr at 4° C. The beads were washed for 3×1 min with 1 ml 1×TBS with 1 mg/ml BSA and recovered by centrifugation at 1.8K rpm to remove excess antibody. Pre-cleared supernatant was added to the anti-AUI beads and incubated for 90 minutes at 4° C. The beads were recovered and washed as before. Sample buffer (Laemmli, 1970) was added, samples were boiled for 3 minutes, and analysed by 12% SDS-PAGE and western blotting with an anti-steA C5/2 monoclonal antibody (Maryland Biosciences).

Gel Filtration

25 µl of approximately 2.5 mg/ml purified recombinant SteA or SteA variant were flowed over a Superose 12 gel filtration column at a rate of 0.04 ml/min using an Akta Prime (Pharmacia). The elution volumes of the SteA variants was compared to calibration standards loaded at a concentration of 0.5 mg/ml.

Circular Dichroism

Aliquots of recombinant SteA, SteA variant or STM containing peptide were purified by NiNTA chromatography and dialysed into 25 mM potassium phosphate buffer overnight at 4° C. Insoluble particulate matter was removed with a 25 µm filter. Circular dichroism analysis was performed using a Jasco J8-10 system at an $A_{280}$=0.2 using a 150 µL quartz cuvette with 0.5 mm path length. Folding spectra were collected from 190 nm to 250 nm, while the presence of beta sheet over a range of temperatures was monitored at 215 nm. 10 spectra were taken for each SteA variant and condition, averaged, then the spectra for buffer alone subtracted to produce the final curves.

Expression and Immunofluorescent Detection of SteA and Variants in Mammalian Cells Human U2OS osteosarcoma (ATCC HTB-96) cells grown on coverslips at a density of $5 \times 10^4$ cells per 6 well dish were transfected with 1 µg plasmid DNA and 3 µL Genejuice (Novagen). 48 hrs after transfection the cover slips were washed three times with PBS and cells fixed for 10 mins at room temperature with 4% paraformaldehyde (BDH, Poole, Dorset) freshly prepared in 1×PBS. After 3 washes with 1×PBS, cells were permeabilized in 1×PBS and 0.1% Triton-X-100 for 10 mins at room temperature and incubated in blocking solution (4.5 ml PBS, 500 µl Foetal Calf Serum [HyClone, Cramlington, Northumberland], 50 mg bovine serum albumin and 0.1% Triton-X-100) for 30 minutes, then in anti-Stefin A antibody (1:100 in blocking solution) overnight at 4° C. The cells were washed 3×5 mins with PBS, incubated in 1:200 anti-mouse Alexa 488 nm secondary antibody (Molecular Probes, Inc) in blocking solution for 1 hour then washed for 3×5 mins in PBS. The coverslips were mounted on slides using Vectashield with DAPI (Vector Laboratories). For pGFP² C2 expressed variants, the cells were transfected as above, but after 24 hrs the cells were washed three times with 1×PBS, then incubated for 4 minutes at room temperature in PKH26 fluorescent membrane stain (Sigma) diluted 1:250 in PBS. Cells were washed 3×5 mins in PBS and fixed with 4% paraformaldehyde freshly prepared in 1×PBS for 10 mins at room temperature. The cells were washed 3×5 mins with PBS and finally the coverslips were mounted on slides using Vectashield containing DAPI (Vector Laboratories). All slides were subsequently analysed by confocal microscopy using the Zeiss LSM 510 Metaconfocal and Zeiss software.

Screen for Peptide Aptamers Binding a Yeast SH3 Domain

Degenerate oligonucleotide cassettes were made by annealing and amplifying P20 and P21 encoding a biased library designed around the Pbs2p proline rich sequence (NKPLPPLPLV) (SEQ ID NO: 33) that interacts with the SH3 domain of Sho1p.

Translation of the cassette gives X(L/V/P/A)N(K/R)PLP(P/S/A)LP(L/V/P/A)X (SEQ ID NO: 34). At the DNA level, this oligonucleotide should give rise to a library with a theoretical complexity of 98,304. The cassette was ligated into STM pJG4-5, and grown up in XL10 Gold cells (Stratagene). The midi-prepped (Qiagen) DNA was used to create a yeast library of $6 \times 10^4$ cells in EGY48, theoretically covering 60% of the sequences encoded by the library. These cells were mated with EGY42 cells carrying pEG202-Shot-SH3, made as described above. Interactors were selected on -UHTL/X-Gal/Gal-Raff plates for 4 days, picked and the plasmids rescued into *E. coli* KC8 cells. The plasmids were transformed back into EGY48 to confirm interaction with the SH3 domain of Sho1p in EGY42 using an interaction-mating matrix.

Papain Binding Assay

Agarose beads carrying carboxymethylated papain (Calbiochem) were washed three times in EB (equilibration buffer: 50 mM sodium phosphate pH 6.5, 0.5M NaCl, 0.1% non-detergent sulfobetaines). The beads were blocked with 1 mg/ml BSA in EB for 30 mins at 4° C. and washed three more times in EB. 300 µg of recombinant SteA or STM AU1 in 1×TBS buffer was diluted into EB to produce a total of volume of 500 µL and incubated with the beads with turning end over end for 90 mins at 4° C. The beads were then washed three times in EB and resuspended in 50 µl of sample buffer for analysis by 12% SDS-PAGE gel and western blotting using an anti-steA monoclonal antibody (C5/2, Maryland Biosciences).

Cathepsin B and Cathepsin H Activity Assays

The activity of recombinant cathepsin B (Innozyme) was measured using the cathepsin B activity assay Kit (Innozyme). We measured the inhibitory activity of SteA and our variants by titrating them into this reaction. Assays were otherwise performed exactly as described by the manufacturer. The same conditions were used to measure the inhibitory activity of SteA and variants against human liver Cathepsin H (Calbiochem) with L-Arginine-7-amido-4-methylcoumarin hydrochloride (Sigma) as substrate. Fluorescence was measured using a Fusion Alpha plate reader (Perkin Elmer).

Example 1

Use of Stefin A as a Scaffold Protein

Figure 1:
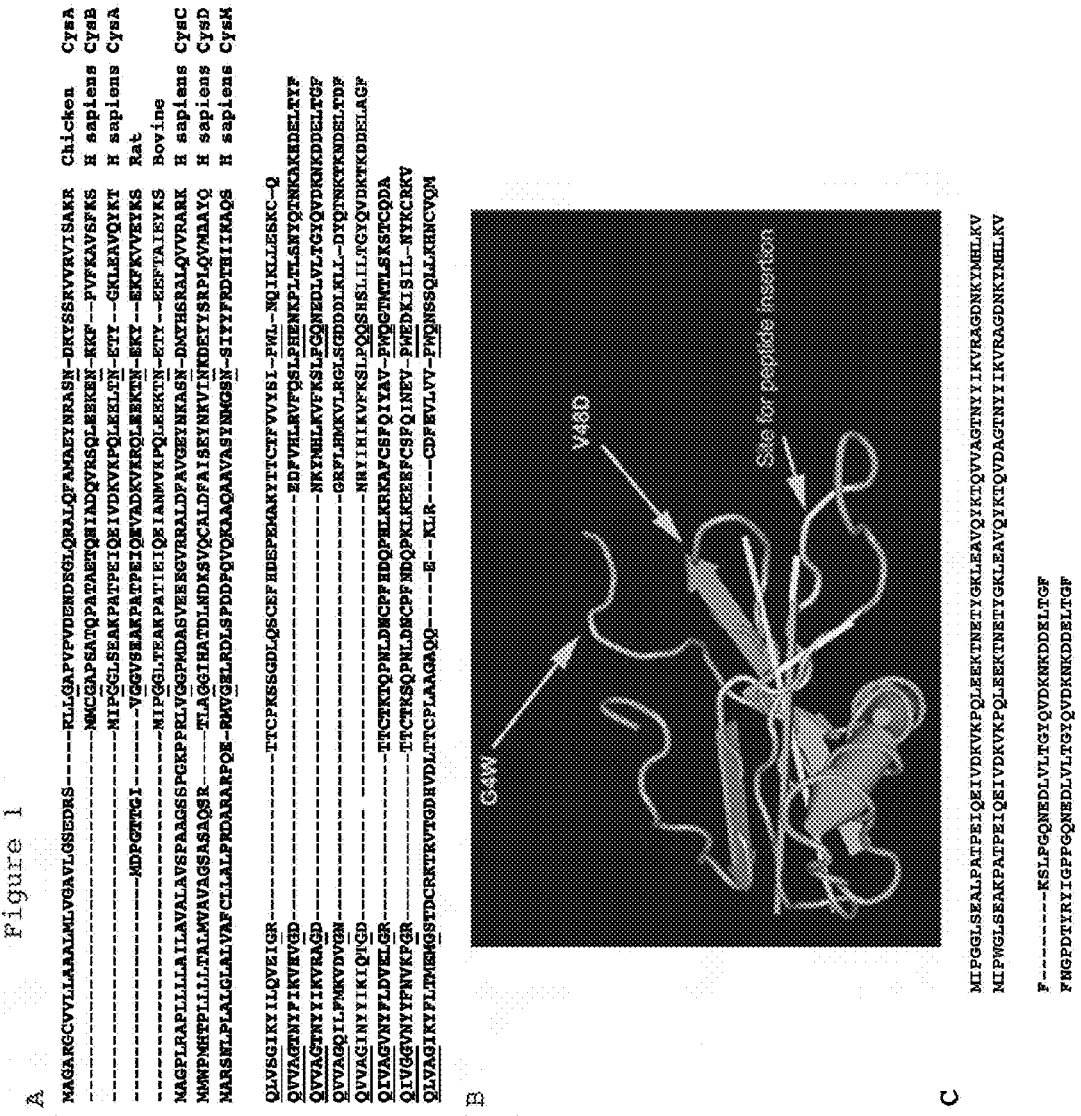
FIG. 1, Panel A. Shows representations of the molecular structure of Stefin A. Panel A: an alignment of Stefin family members across evolution identifies regions of high and poor conservation that may correspond to structurally and functionally important regions. Additional amino acid residues present in family members are shown in gold. Conserved residues that are known to be important for protein-protein interactions that we have altered are highlighted in red, while the site of peptide insertion is shown in blue. NCBI sequences NP_005204 (human cystatin A) (SEQ ID NO: 117), NP_000091 (human cystatin B) (SEQ ID NO: 116), P01034 (human cystatin C precursor) (SEQ ID NO: 120), NP001891 (human cystatin D precursor) (SEQ ID NO: 121), NP_001314 (human cystatin M precursor) (SEQ ID NO: 122), as well as the sequences for chicken (NP990831) (SEQ ID NO: 115), rat (XP213617) (SEQ ID NO: 118) and bovine (P80416) (SEQ ID NO: 119) cystatin A were aligned using ClustalW of the GCG suite. Panel B: a representation of the NMR solution structure of Stefin A, created using Cn3D software and PDB coordinates 1DVD (Martin et al. 1995 'The three-dimensional solution structure of human stefin A.' J Mol Biol. vol 246 pp 331-43). The regions that were mutated to produce STM are highlighted in yellow.

FIG. 1 shows the primary amino acid structure of parts of Stefin A and its homologues. FIG. 1*b* shows three dimensional structure of Stefin A. FIG. 1*b* also shows the three sites in Stefin A which are mutated in order to facilitate its use of the scaffold protein. These are G4W, V48D and Leu 73 which is shown as 'site for peptide insertion' in FIG. 1*b*.

A Stefin A polypeptide for use as a scaffold protein is produced by mutating the sequence of Stefin A as described. The resulting protein based on Stefin A but possessing those three mutations is termed STM. The sequence of STM is given in the attached sequence listing.

FIG. 2*a* shows the heat stability of STM. As can be seen from FIG. 2*a*, STM is stable to 70° C., where it starts to unfold. Unfolding is complete at 98° C., but STM refolds to its correct form upon cooling to 25° C. even when bearing a 20 amino acid target peptide insertion.

FIG. 2b demonstrates that the scaffold protein STM presents the target peptide to solvent. This is demonstrated by immunoprecipitation experiment demonstrating that the anti peptide antibody (anti-AU1) can access the target peptide when inserted into STM scaffold for expression.

Example 2

STM is Biologically Neutral

Stefin A is known to form dimers. Use of Stefin A as a scaffold protein advantageously abolishes dimerisation. As can be seen from FIG. 3, the STM scaffold protein has abolished dimerisation and is shown to be monomeric.

It is the V48D mutation which is responsible for the abolition of dimerisation. In some embodiments, it may be advantageous to retain dimerisation ability. For example, it may be useful to be able to heat shock the system and induce dimerisation of scaffold protein according to the invention. In this embodiment, the V48 amino acid should not be mutated. Thus in this embodiment the invention would relate to a double mutant Leu 73 and G4W. This scaffold protein would still advantageously allow a dual surface approach and offers the additional benefit of a heat inducible dimerisation. One application of such a scaffold protein would be in investigating mode of action within a signalling pathway. For example, by inserting two different target peptides into two separate scaffold protein molecules, these could be conveniently brought together by heat shocking a cell containing them both, resulting in dimerisation and association of the two target peptides. This can have the further advantage of bringing together cellular proteins that are bound to the peptides.

Biological neutrality is an advantage of the present invention since it does not exist in the prior art scaffold proteins. One aspect of the biological neutralisation of Stefin A according to the present invention is to abolish the papain binding of Stefin A. Papain is a founder member of the cathepsin family. As can be seen from FIG. 4, the Stefin A based scaffold protein STM does not interfere with cathepsin activity.

Figure 5:
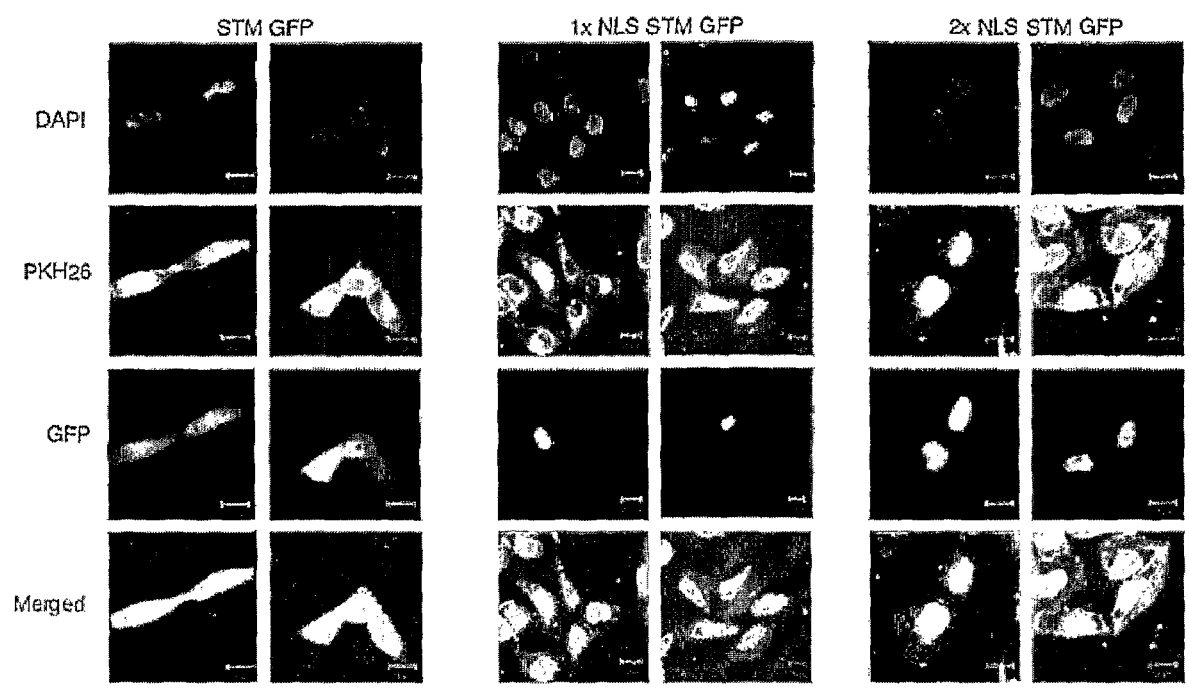
FIG. 5 shows photomicrographs of cells. STM can present biologically functional peptides in the context of mammalian cells. STM fused to GFP localises throughout the cytoplasm and nucleus of U2OS cells (left hand column). However, once one (middle column) or two (right hand column) NLS peptides are inserted into the peptide-accepting site engineered into STM, the peptide aptamer-GFP fusion localises exclusively to the nucleus. Cells were counterstained with DAPI (top row) to reveal the nucleus and with the membrane dye PKH26 to show the plasma membrane (second row). STM-GFP fusions without and with NLS peptides are shown in the third row of pictures, and all three images are overlaid in the final row.

Stefin A has a cytoplasmic anchor/nuclear export sequence. Thus, Stefin A cannot usually access the nucleus. This biological property of Stefin A has been abolished in Stefin A based scaffold proteins according to the present invention such as STM. This is demonstrated in FIG. 5 which shows that STM can go into the nucleus when it bears a nuclear localisation signal, whereas Stefin A cannot.

Example 3

Demonstration of Use of Stefin A as a Scaffold Protein

There are a number of known CDK2 binding peptide aptamers in the art. Some of these peptide aptamers are known to inhibit CDK2 activity. In order to demonstrate utility of the invention, some of these aptamers have been compared in the setting of a Stefin A based scaffold protein according to the present invention and in the setting of the prior art scaffold protein such as thioredoxin A.

Figure 6:
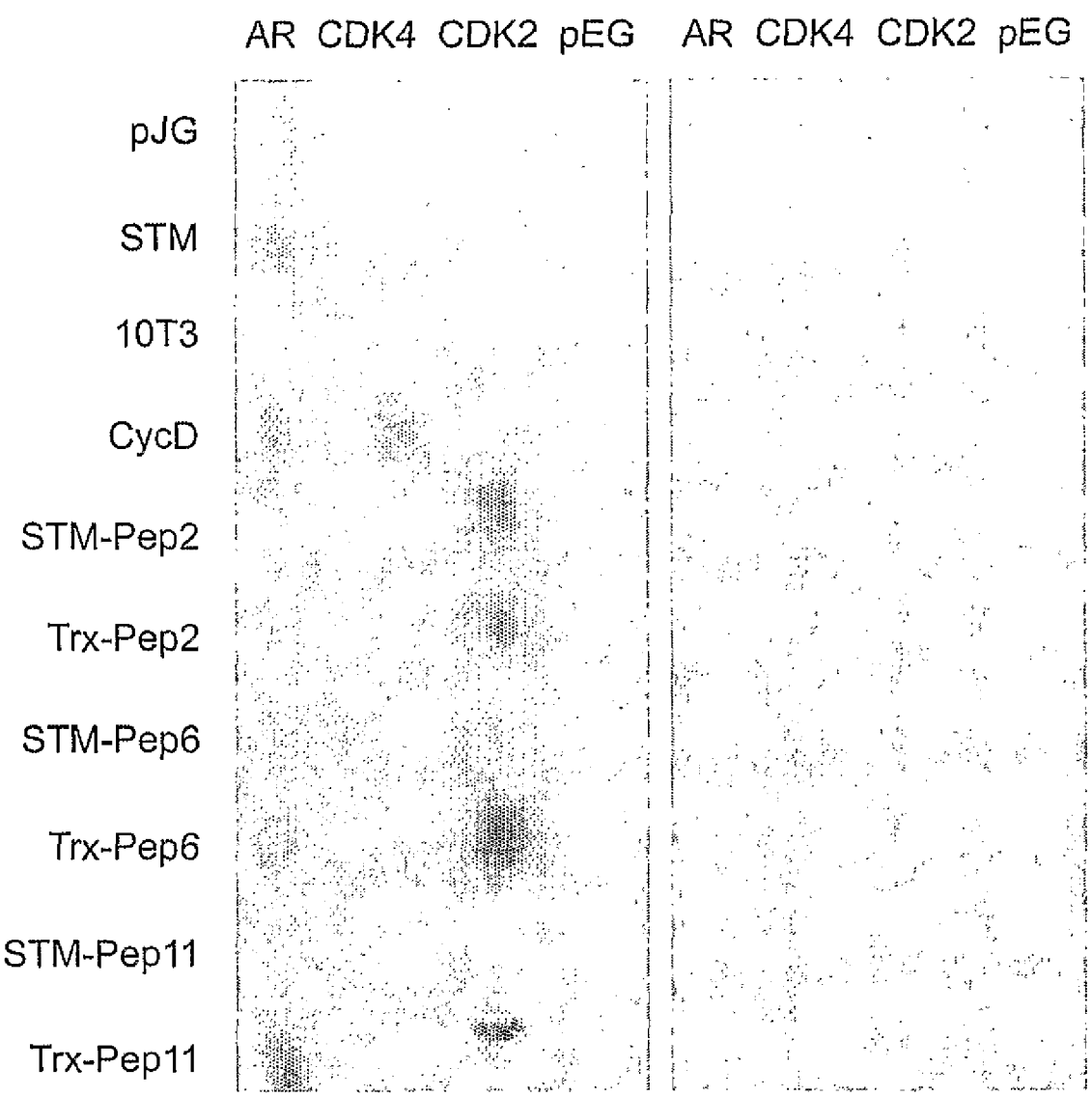
FIG. 6 shows photographs of developed cell patches. CDK2 interacting peptides can be moved from thioredoxin to STM. Fourteen peptide aptamers identified in a screen for peptide aptamers constrained by thioredoxin (Trx) that could bind to CDK2 were shuffled from Trx to STM. Of these, only two (Pep2 and Pep6) could still recognize CDK2. Pep11 is shown as an example of a peptide that binds CDK2 when presented by Trx, but not by STM.

Considering FIG. 6, it can be seen that results achieved with Stefin A can be different to those achieved with the prior art scaffold thioredoxin A. This demonstrates that three dimensional peptide space can be explored using Stefin A based scaffolds which cannot be explored using TrxA based scaffolds.

Example 4

Production of Scaffold Protein

Here, we describe a rational approach to the design of a new peptide aptamer scaffold. We outline the qualities that an ideal scaffold would need to possess to be broadly useful for in vitro and in vivo studies and apply these criteria to the design of a new scaffold, the preferred example being STM.

Starting from the small, stable intracellular protease inhibitor Stefin A, we have engineered a biologically neutral scaffold that retains the stable conformation of the parent protein. We show that STM is able to present peptides that bind to targets of interest, both in the context of known interactors and in a library screen. Molecular tools based on our scaffold find application in a wide range of studies of biological pathways, and in the validation of drug targets.

Human Stefin A as the Parental Protein for a New Scaffold

We selected a panel of 8 candidate proteins (*Sulfolobus solfataricus* TBP; the red fluorescent protein of *Discosoma* spp., dsRED2 and humanized green fluorescent protein from *Renilla reniformis; Saccharomyces cerevisiae* Gcn4p and *H. sapiens* Stefin A) or protein domains (Gcn4p core, comprising the leucine zipper and the DNA binding region; and triple helical coiled coil repeats from human utrophin and dystrophin). These were cloned into expression vectors and expressed in tissue culture cells under the control of the CMV promoter. Of these candidates, only human Stefin A (SteA) was both readily detectable by western blotting and lacked toxicity in human cells, suggesting that it might be engineered to be a good scaffold. SteA is a monomeric, single domain protein of 98 amino acids that receives no known post-translational modification and lacks disulphide bonds. SteA shows remarkable thermostability with a reversible transition observed at 90.8° C. and folding enthalpy of 490 kJ/mol, all important features of a SteA-based scaffold.

Choice of Site for Peptide Insertion

We aligned the protein sequences of human SteA, SteB, Cystatin C precursor, Cystatin D precursor, Cystatin M precursor, as well as rat, bovine and chicken Cystatin using Clustal W of the GCG suite and then manually adjusted the alignment to take into account topological features (FIG. 1A). Poorly conserved regions are unlikely to contribute to protein folding, while highly conserved domains may mediate biological interactions. SteA structures (FIG. 1B) have identified which residues are involved in target protease binding and which residues constitute the hydrophobic core of the SteA. The leucine residue at position 73 mediates part of the interaction between SteA with its target proteases. Various members of the cystatin family have insertions close to this region (FIG. 1A). Specifically, the insertions are short or lacking in family I members (of which human Stefin A is a member) but are present in chicken cystatin A (family II member) as well as, for example, cystatin M indicating that SteA may accept the insertion of peptides at this point. The structure of chicken cystatin A suggests that peptides inserted here are likely to be well constrained, yet able to adopt a range of conformations including α-helix and β-strand and that Leu 73 and the residues surrounding it play no role in the structural folding of SteA. Thus we reasoned that introduction of a peptide at this point should allow constraint of the inserted sequence without disrupting the folding of the scaffold, and ensure presentation of the peptide to solvent. We introduced an RsrII restriction endonuclease site into the SteA open reading frame at the codons corresponding to residues 72, 73 and 74, so as to allow the subsequent insertion into the open reading frame (ORF) of oligonucleotides encoding peptides to be constrained by the scaffold. We refer to the protein encoded by the mutant ORF as RS (RsrII SteA). We also wished to eliminate known protein-protein interactions. Glycine 4 (highlighted in FIG. 1), a structural determinant of Stefin A's binding to target proteases, was mutated to tryptophan and valine 48 was mutated to aspartate. The latter change should both decrease interactions with target proteases and reduce the scaffold's propensity to dimerize through domain swapping. We refer to the engineered protein with all of these mutations as STM (Stefin A Triple Mutant; see sequence listing). An illustration of the sequence of the mutated protein with a model sequence (the AU1 peptide, see below) aligned with human stefin A is shown in FIG. 1C.

Example 5

Expression of SteA Scaffolds in Mammalian Cells

Wild type Stefin A is predominantly cytoplasmic which could limit the usefulness of the new scaffold. Cytoplasmic localisation can be the result of nuclear exclusion (by size or by active nuclear export) or cytoplasmic anchoring, where the protein is physically restricted to a cytoplasmic locale by virtue of tight interactions. Inspection of the SteA sequence did not identify any homology to known nuclear export sequences. We asked whether the mutations, by causing loss of protein-protein interactions, affected this localisation. When transfected into U2OS osteosarcoma cells RS also localizes predominantly to the cytoplasm as shown in the following table:

TABLE

Sub-cellular localisation of SteA variant proteins. Percentages are given for the number of cells expressing SteA variant proteins showing the listed localisation.

|  | Either cytoplasmic or limited nuclear availability | Equal nuclear/cytoplasmic | Nuclear |
|---|---|---|---|
| RS | 33% | 67% | 0% |
| STM | 20% | 80% | 0% |
| NLS-STM | 5% | 0% | 95% |

Further engineering to STM led to nuclear and cytoplasmic localisation (see table), indicating that if there is an unidentified nuclear export signal in SteA, it has been disabled by our engineering. The addition of a single SV40 Large-T NLS (PKKKRKV) (SEQ ID NO: 31) to the amino-terminus of STM resulted in complete nuclear localisation of STM (see table), but not of the RS protein. Together, these data indicate that (i) the small SteA protein is not excluded from the nucleus by size exclusion limits imposed by the nuclear pore complex; (ii) that active nuclear export is unlikely to be operating, and therefore that (iii) the predominant cytoplasmic localisation of SteA is mediated at least in part by cytoplasmic interactions that we have abolished in STM. Thus STM can be stably expressed in human cells and we have abolished SteA's normal interactions.

Example 6

SteA Based Scaffolds are Stable

We wished to ascertain whether we could insert peptides into STM without affecting its stability as a protein. We modelled a peptide aptamer by inserting the six residue "AU1" epitope tag (DTYRYI) (SEQ ID NO: 32) into the engineered loop. We wished to retain the thermostability of SteA but abolish its dimerization by domain-swapping, which is enhanced by heating. We incubated recombinant SteA, STM and STM AU1 at 75° C. or on ice for 20 minutes, and removed any denatured protein by centrifugation. Essentially all of the heated SteA and engineered STM protein was recovered, indicating that STM has retained the thermostability of SteA (FIG. 2, panel A) and that STM is able to present at least one peptide without the folding of the scaffold being adversely affected, at least partially satisfying our second criterion. The dimeric form of wild type SteA can be seen in the unheated sample (FIG. 2A, left-hand panel, asterisk), increasing significantly following heat treatment (FIG. 2A, right hand panel). As expected, this dimeric form is completely abolished in both STM and STM AU1 (FIG. 2A).

We also asked whether the AU1 peptide in STM was available for interaction. An anti-AU1 antibody was able to specifically immuno-precipitate recombinant STM AU1 from cell lysates (FIG. 2B). A saturating level of anti-AU1 antibody could immuno-precipitate all of the input STM (compare lanes 6 and 7), indicating that all of the detectable STM AU1 was presenting inserted AU1 epitope for interaction. The ability of STM to present linear epitope sequences that can be specifically recognised by a cognate antibody is a key feature of a scaffold according to the present invention.

Example 7

Biophysical Characterisation of Stefin A Mutants

To confirm that the engineered scaffold was correctly folded, we used gel filtration chromatography to ask whether we could detect any denatured or dimerized STM in its native form. Recombinant STM AU1 migrated close to its predicted size and similarly to wild type SteA (FIG. 3, panel A). When the protein preparations were heated to 75° C. before gel filtration, a proportion of SteA migrated as a dimer. Importantly, as predicted, STM AU1 did not. We also confirmed that STM and SteA possess similar folding patterns by circular dichroism (CD), which allows the determination of the α-helical and β-sheet content of a folded polypeptide. The CD spectra of native SteA at 25° C. and 50° C. and native STM AU1 at 25° C. and 50° C. (FIG. 3B) are all very similar and differ significantly from the control spectra of the denatured STM AU1 obtained at 97° C. The common lower inflexion point at 216 nm (which is characteristic of β sheet; SteA has 5 antiparallel β strands) and the overall similarity of the curves provide evidence that STM/AU1 is correctly folded, further indicating that STM is likely to perform well as a peptide aptamer scaffold.

Example 8

Neutrality Assays

Protease Effects

Figure 4:
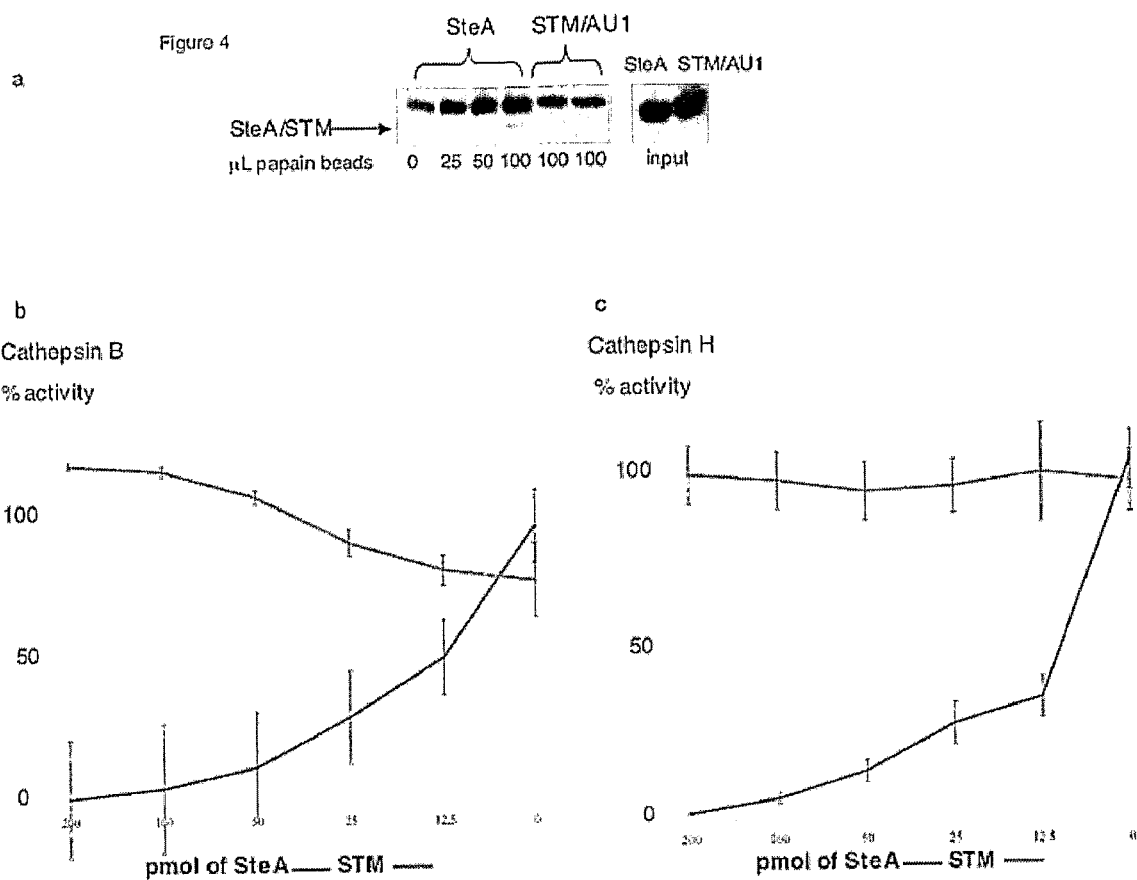
FIG. 4 shows graphs and blots which show that STM (unlike SteA) is no longer able to bind to its former partners, the cathepsins, or papain. Panel A: Equal amounts of purified recombinant SteA or STM with an AU1 insert (indicated by the arrow) were incubated with papain-agarose beads. Proteins that bound to the beads were separated by SDS-PAGE and SteA variants detected with an anti-SteA antibody. A cross-reacting protein that originates on the beads shows equal loading of the lanes. SteA is able to bind to beads. In contrast, STM does not co-purify with the beads, as shown by the duplicate empty lanes. Panel B: the ability of SteA to inhibit the protease activity of cathepsin B decreases as SteA is diluted. Even the highest levels of STM/AU1 are without effect. Panel C. shows the same effect as panel B, but using cathepsin H as the protease that can be inhibited in a concentration-dependent fashion by SteA, but whose activity is unaffected by even high levels of STM/AU1.

Wild-type stefins are inhibitors of the protease activity of the cathepsin family, of which papain is the founder member. To confirm that our engineered mutants lacked biological activity, we asked whether STM could bind to papain, or inhibit cathepsin activity. Immobilized papain was able to affinity purify SteA, but not STM, in a concentration-dependent manner (FIG. 4A). Moreover, the activity of cathepsin B (FIG. 4B) and cathepsin H (FIG. 4C) was inhibited by the addition of SteA whereas even high concentrations of STM did not inhibit this activity (FIG. 4).

Nuclear Import

We extended our experiments to human cells, asking for interaction with the nuclear import machinery. One or two contiguous NLS sequences were inserted into the engineered peptide insertion site of the scaffold (in contrast to the experiment described in Example 5, where the NLS was placed at the amino terminus). Whereas STM-GFP localises throughout the cell (Table in Example 5 and FIG. 5), clear and exclusive nuclear localisation can be observed for both the single and double NLS STM variants. This is clear evidence that STM can present peptides 6 or 14 residues in length that can bind the nuclear import machinery in human cells.

Example 9

Peptide Aptamer Interactors with a Defined Target

The first peptide aptamer screen identified 14 peptide sequences that, within the context of the now traditional *E. coli* thioredoxin scaffold, all bound to human CDK2. We wished to ask whether STM was able to present any of the same peptides for interaction. Our interaction matrices include a set of standard controls that allow us to make comparisons between experiments. These are the androgen receptor, a natural transcriptional activator that controls for reporter gene activity and plate performance; the naturally interacting pair of CDK4 and cyclin D, which control for yeast mating and two hybrid interactions; and the weakly interacting pair of CDK4 and 10T3, a peptide aptamer that was identified as a specific interactor with cyclin D that fails to produce a robust phenotype in cells. Of the 14 CDK2-interacting peptides tested, only two (Pep2 and Pep6; FIG. 6) were able to recognise CDK2 when presented by STM. Of these, Pep2 had apparently higher affinity in this assay for CDK2 in the context of STM, as these cells developed a blue colour sooner than those expressing Pep2 in thioredoxin. This could simply be due to increased stability of the STM-based peptide aptamer, or it could be due to an altered conformation of the peptide in STM, In contrast, Pep6 in STM clearly shows much lower affinity for CDK2 than in TrxA. None of the peptide aptamers in STM gained affinity for CDK4. These data suggest that STM will be able to present a different range of peptides for interaction than thioredoxin, although there will be some overlap.

Example 10

Identifying a Target Peptide Capable of Binding a Structure of Interest

Finally, we wished to complete the validation of our new scaffold by showing that it is able to present constrained peptides that could bind to a defined structure of interest, in this case a target protein in a library format. The SH3 domain has been extensively studied and is known to bind PxxP motifs of partner proteins. A degenerate peptide aptamer library with a theoretical size of 38,400 different peptide sequences was screened for those that would bind to the Sho1p SH3 domain. Fourteen different constrained peptides were identified in this screen, some of them multiple times; see table below:

TABLE

Peptide Aptamers in STM that interact with the SH3 domain of yeast Sho1p.

| | Sequence | | Times identified |
|---|---|---|---|
| 01: | GPVPNKPLPALPVIGPGVNKPLPALPAHGPIRNKPLPSLPASGP | (SEQ ID NO: 36) | 3 |
| 02: | GPVLNKPLPSLPVMGPTPNKPLPPLPAAGP | (SEQ ID NO: 37) | 4 |
| 03: | GPDLNKPLPALPVHGP | (SEQ ID NO: 38) | 1 |
| 04: | GPYLNRPLPSLPAYGPWVNRPLPSLPLSGP | (SEQ ID NO: 39) | 3 |
| 05: | GPNLNKPLPALPVLGP | (SEQ ID NO: 40) | 1 |
| 06: | GPVVNKPLPSLPVKGPDVNKPLPSLPAVGP | (SEQ ID NO: 41) | 1 |
| 07: | GPPNVKPLPALPLMGPLLNKPLPALPLDGP | (SEQ ID NO: 42) | 1 |
| 08: | GPDPNRPLPSLPVTGPYLNKPLPALPVSGP | (SEQ ID NO: 43) | 1 |
| 09: | GPMLNKPLPSLPVGGPGLNKPLPSLPAAGP | (SEQ ID NO: 44) | 3 |
| 10: | GPILNKPLPALPLRGPDPNRPLPALPVTGP | (SEQ ID NO: 45) | 2 |
| 11: | GPFPNKPLPALPLTGPVLNRPLPPLPRNGP | (SEQ ID NO: 46) | 3 |
| 13: | GPYLNKPLPSLPLCGPSVNRPLPALPDVGP | (SEQ ID NO: 47) | 2 |
| 17: | GPEPNKPLPALPLTGPVLNRPLPPLPRNGP | (SEQ ID NO: 48) | 2 |
| 20: | GPRMNKPLPSLPLGGPAMNKPLPALPLQGP | (SEQ ID NO: 49) | 1 |

The wild type Pbs2p sequence that naturally interacts with this SH3 domain is "NKPLPPLPLV", (SEQ ID NO: 33) and the library peptide was designed as "gpX(L/V/P/A)N(K/R)PLP(P/S/A)LP(L/V/P/A)Xgp" (SEQ ID NO: 35), where lower case residues are contributed by the RsrII/AvaII sites used for cloning oligonucleotides encoding the peptide, and X is any amino acid.

These data indicate that STM can function as a scaffold for the presentation of peptides ranging from 12 to 36 residues in length, adding further breadth to its future applications.

Example 11

Using Peptide Aptamer to Disrupt Domain-Ligand Interaction

We wished to use peptide aptamers to map SH3 domain interactions. Referring to FIG. 7, as a first model, we chose the SH3 domain of the putative yeast osmo-sensor Sho1p (yellow). Peptide aptamers that bind to the SH3 domain may be expected to interfere with signalling in yeast cells. For example, interaction of a peptide aptamer (red) with the SH3 domain in yeast may prevent association with the MAP kinase kinase Pbs2p, which itself also serves as a specificity scaffold directing signals from the MAPKKK Ste11 to the MAPK Hog1.

Peptide Aptamer Cause Osmo-Sensitivity in Budding Yeast.

Signalling through the Hog1 pathway is required for yeast cells to grow on high osmolarity media containing 1M NaCl or 1 M sorbitol. PepA, 32, 34, 124 and 201 were all isolated from the yeast two hybrid screen for peptide aptamers that would bind to the SH3 domain of Sho1p. Of these, only PepA is able to confer osmo-sensitivity to yeast cells when its expression is induced on media supplemented with galactose. Cells grown on glucose do not express the peptide aptamers, and are osmo-resistant. See FIG. 7B.

Hog1 Activation is Impaired in Yeasts Expressing PepA.

The most likely mechanism for PepA to be conferring osmosensitivity on yeast is by interrupting signalling from Sho1p, via Pbs2 to Hog1. To ask whether this was happening, we used the an anti-phosphotyrosine antibody to monitor Hog1p activation. When cells are grown on high osmolarity medium, Hog1p is phosphorylated (control, − and + galactose). The expression of a peptide aptamer that does not confer osmo-sensitivity does not affect Hog1 phosphorylation (Pep32), whereas the induction of PepA by galactose almost completely abolishes the phosphorylation and activation of Hog1 in cells, explaining their sensitivity to hyperosmolarity. See FIG. 7C.

PepA Disrupts the Physical Association Between Sho1p and the Pbs2/Hog1 Complex.

PepA shows significant identity with both Las17 (an organiser of the actin cytoskeleton implicated in interactions with Sho1) and Pbs2, the MAPKK and scaffold protein that phosphorylates and activates Hog1p. In principle, it could therefore interfere with signalling via either arm of the model schema shown. However, GST-pull downs using the Sho1 SH3 show an interaction between Sho1 and Hog1, unless PepA is present, suggesting that PepA does indeed interrupt the interaction between Sho1 and Pbs2. See FIG. 7D.

Thus it is shown that scaffold proteins of the present invention present peptides in correct biological conformation.

Example 12

Presentation of Target Peptide to Solvent

As a further test of function of scaffolds of the present invention, we wished to ask whether a scaffold according to the present invention could present a peptide to solvent in a form that could be phosphorylated by a protein kinase. In this example the scaffold is STM.

Oligonucleotides encoding the PKA/PKB phosphorylation site of c-Raf were cloned into the RsrII site of STM (FIG. 8a). The resulting peptide aptamer, called here STM-pRaf, was well-expressed in both yeast and human cells, and could be detected using an antibody specific for c-Raf phosphorylated at the PKA/PKB site.

Figure 8:
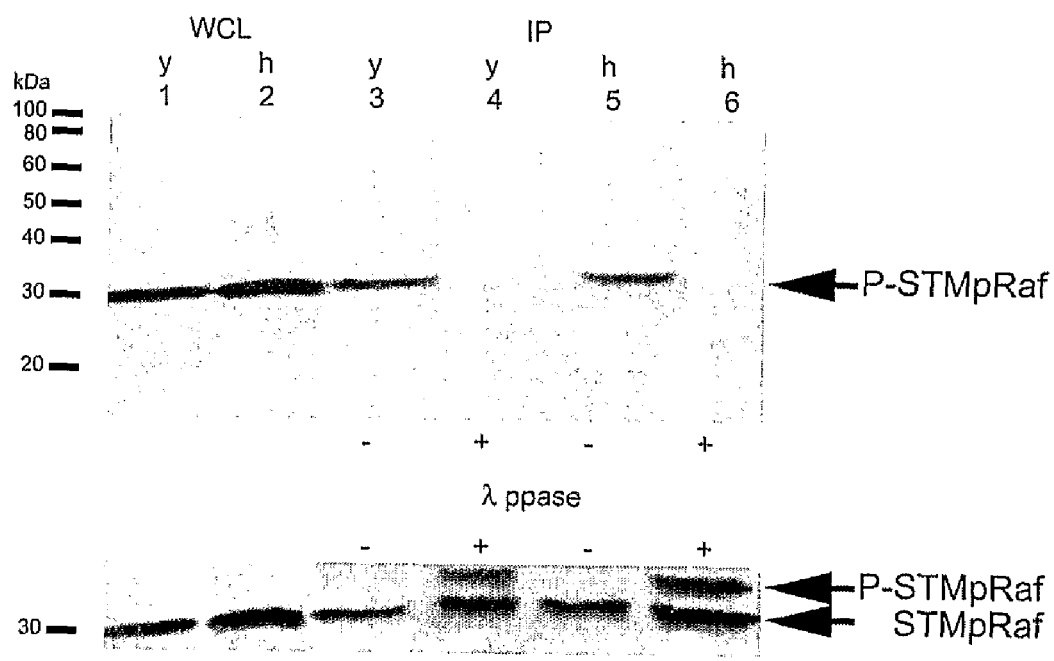
FIG. 8 shows photographs of kinase assays.

Regarding FIG. 8, Panel a shows oligonucleotides encoding the PKA/PKB phosphorylation site of c-Raf were cloned into the RsrII site of STM, to create STMpRAF. The phosphorylated serine is underlined. Panel b: an antibody that recognises phosphorylated c-Raf was used to probe western blots of whole cell lysates (WCL) and anti-myc immuno-precipitates (IP) from yeast (y) or human (h) cells expressing myc-tagged STMpRaf. Treatment of the immuno-precipitated protein with 100 units of λ phosphatase causes the signal to disappear. Panel c: λ phosphatase treatment specifically causes dephosphorylation of STMpRaf, rather than degradation of the STMpRaf protein.

Immuno-precipitation of myc-tagged STM-pRaf confirmed the identity of the band as STM-pRaf, rather than contaminating c-Raf. To confirm that the signal generated by the anti-cRaf antibody was due to protein phosphorylation, rather than deformation of the peptide induced by the scaffold, we treated the immuno-precipitates with λ phosphatase. The signal was lost following dephosphorylation, and anti-myc western blots confirmed that this was not due to protein degradation, and that the c-Raf peptide was indeed being presented by STM for phosphorylation by cognate protein kinases inside yeast and human cells.

Thus the scaffolds of the present invention advantageously present peptides in a form in which they are recognised by their cognate signalling partners.

Example 13

Re-Wiring a Signaling Network Using an Artificial SH3 Domain Ligand

This example demonstrates use of peptide aptamers according to the present invention as artificial signaling modules.

Overview

Genome-wide gene expression microarrays identify genes whose altered expression correlates with disease, but not which of these gene products are candidate drug targets. While RNAi may allow the validation of a sub-set of these, "knock-out" techniques overlook the contributions of specific protein-protein interactions. The ready availability of engineered proteins, such as peptide aptamers, that can directly compete for protein-protein interactions in cells would greatly facilitate drug target validation. Here, we describe a robust and highly specific technology to show how peptide aptamers may be used to dissect protein interactions in cells. We uncover a previously unidentified role for an essential protein in a non-essential pathway, indicating that this technology may usefully supplement RNAi in drug target validation efforts.

Introduction

The sequencing of the human genome and the subsequent use of genome-wide screens (whether using RNAi or microarrays) have led to the association of many gene products with various diseases. A major challenge is to determine which of these gene products are valid drug targets. In the case of proteins that function within cells, this requires an understanding of the protein's behaviour both in the pathological and the healthy situation. One solution to this problem would be to devise a molecular toolkit that could be adapted to the study of each protein in the cellular context. We propose that toolkits of engineered proteins using peptide aptamers as unique recognition domains can be created. Peptide aptamers are selected in yeast two hybrid screens for binding to a protein of interest. A proportion of binders are able to compete in vivo for protein-protein interactions, leading to measurable phenotypes. Where the phenotype is the reversal of a disease phenotype, the peptide aptamer has both validated the drug target, and provided the basis for drug identification, whether by structure based drug discovery from a co-crystal, or by drug displacement screening. In addition, each peptide aptamer could be the recognition domain for an engineered protein; this would be most useful where the peptide aptamer itself does not lead to a phenotype when expressed in cells. Each recognition domain would be genetically fused to one of several effector moieties, such as GFP or the catalytic moiety of an enzyme such as a protease or an ubiquitin ligase. While the latter may remove a target protein altogether as has been demonstrated for engineered F-box proteins, fusions to GFP would allow monitoring of a protein's intracellular trafficking, with the added potential for monitoring specific protein-protein interactions in cells by FRET. Beyond cell biology, fusions of a peptide aptamer to GST would allow the integration of information gained using cell biology techniques with the biochemical and structural analysis of any given protein. Although peptide aptamers represent a useful source of recognition moieties, alternative technologies (based on staphyloccal nuclease or GFP, or termed affibodies, monobodies, anticalins, or designed ankyrin repeat proteins) may also prove useful.

Progress towards these goals has been partly hampered by the need to demonstrate in vivo specificity. Recently, there has been some interest in designing molecular switches that either re-engineer signal transduction events, or seek to create de novo signaling pathways. To date, such studies have typically used protein domains from natural proteins. Here we use peptide aptamers to show that the artificial targeting module can be used to both disconnect and re-connect a specific pathway. This sets a new standard for defining the specificity of action of a peptide aptamer. Where a peptide aptamer's target is known, purification of the target protein from cells expressing the peptide aptamer or a negative control should allow the identification of proteins that are competed from the complex by the peptide aptamer. Here, we show for the first time that this concept can be carried into practice. We describe the first application of our STM scaffold to the in vivo analysis of a signal transduction cascade in yeast, namely the HOG (Hyper-Osmolarity Glycerol) osmotic resistance pathway. We show that a peptide aptamer, AptA, selected for its ability to bind to the SH3 domain of the osmo-sensing protein Sho1, can inhibit Sho1 function. We show that this is achieved by mimicking the natural interaction with Pbs2, a MAP kinase that normally interacts with the SH3 domain of Sho1. We demonstrate the specificity of the interaction by showing first that AptA does not bind to any of the other 27 SH3 domains in yeast cells, and second that a fusion to AptA can restore function to a mutant Pbs2 that cannot otherwise bind to Sho1. In addition to proving that peptide aptamers do have the required characteristics of specificity and flexibility to form the basis for a molecular toolkit, our characterisation of AptA leads us to implicate the WASp homologue Las17 in the osmo-sensing pathway—an implication that had not arisen from exhaustive genetic screening. Thus the invention provides the use of a WASP polypeptide, preferably Las17, in the modulation of a MAP kinase signalling pathway, in particular the Hog MAP kinase pathway. The invention also relates to use of AptA in the treatment of Wiskott-Aldrich Syndrome. Our results also suggest that interaction between Sho1 and Ste11 is not sufficient for signalling in the absence of Pbs2, as has been proposed previously.

Results

The yeast transmembrane protein Sho1 has been shown to be important in the regulation of osmotic stress signaling through its SH3-domain mediated interaction with the MAPKK Pbs2. We predicted that peptide aptamers that bind to the Shot-SH3 domain may inhibit the osmotic stress response. In vitro studies using free peptides have shown that SH3 ligands comprise left-handed polyproline type II helices whose binding to a range of SH3 domains can be promiscuous. This study was therefore also designed to test the ability of our newly designed scaffold (in this example, STM) to present peptides with a high degree of specificity.

To efficiently target peptide aptamers to the Sho1-SH3 domain, a proline rich sequence from Pbs2 MAPKK, already known to be a Sho1-SH3 ligand was used as a template to design a small, degenerate peptide library. The 10 residue-long Pbs2 proline rich sequence "VNKPLPPLPV" (SEQ ID NO: 50) (with the two key prolines underlined) was partially randomized (Table I). The anchoring prolines were retained, to ensure binding to the SH3 domain, while an extra residue was added at either end of the Pbs2 sequence to create a library of 12mer peptides. The positively charged lysine residue was allowed to vary to arginine which is widely found in SH3 domain binding peptides. Other positions were allowed to vary based on mutagenesis studies of Pbs2 and the residues added at each end of the Pbs2-derived 10mer were allowed complete freedom to vary. For comparison, the sequences of other SH3-interacting peptides are also given in Table I. Oligonucleotides encoding these peptides were ligated into the open reading frame of STM, a preferred scaffold according to the present invention, to create a library where the theoretical peptide complexity was $6 \times 10^4$. Screening this library allowed the identification of twenty-eight peptide aptamers as Sho1-SH3 binders. (see above and Table II). Of these, only two (Apt03 and 05) were the expected 12mer peptide constrained within the scaffold. Three others were 11mer peptides where the oligonucleotide encoded an in-frame stop codon (AptA, Apt32, and Apt124), while a further three were unconstrained as the result of a frame-shift in the coding oligonucleotides altering the reading frame until an out-of-frame stop codon in the STM ORF is encountered (Apt34, 40 and 94). Interestingly, peptide aptamers were equally well expressed regardless of insert size (FIG. 13). The high proportion of unconstrained or long, less-well constrained peptides selected in the screen was striking, given that quality control of the library showed that 27 of 33 oligonucleotides for which sequence was determined encoded constrained peptides of the expected length. The selection pressure in this screen is consistent with the previous observation that SH3 domains exert a strong preference for peptides that are not rigidly structured, and suggests that SH3 domains may normally interact with unconstrained stretches such as flexible hinges in partner proteins.

Identification of a Peptide Aptamer that Confers Osmo-Sensitivity.

Peptide aptamers interacting with Sho1 were tested for their ability to block osmo-resistance in yeast cells reliant on the Sho1 branch of the osmo-sensing machinery [Posas F, Saito H. 1997. Osmotic activation of the HOG MAPK pathway via Ste11p MAPKKK: scaffold role of Pbs2p MAPKK. *Science.* 276: 1702-5]. Only one of the twenty-eight SHO1-SH3 binders, a peptide aptamer designated AptA, caused osmo-sensitivity when cells were plated on media containing 1M NaCl (FIG. 9, panel A). AptA, but not control peptide aptamers such as Apt32, also prevented the activating tyrosine phosphorylation of Hog1 on high osmolarity medium (FIG. 9, panel B).

Other peptide aptamers, including Apt32, similarly do not inhibit osmo-resistance (FIG. 9, panel A). None of these peptide aptamers affected yeast growth on media of normal osmolarity. This observation confirms that peptide aptamers are capable of inhibiting protein-protein interactions in eukaryotic cells.

AptA Shows High Specificity for the Sho1 SH3 Domain

It was important to show that AptA is acting at the level of Sho1 SH3, as many PxxP ligands cross-react with more than one SH3 domain in vitro, although specificity seems to be maintained in vivo. For example, of the 28 SH3 domains in the yeast proteome, Pbs2 interacts only with that of Sho1. Furthermore, when the core PLPPLP (SEQ ID NO: 90) sequence of Pbs2 was changed to PLPALP (SEQ ID NO: 91) or PLPSLP (SEQ ID NO: 92), increased promiscuity was observed. Because AptA contains a core PLPSLP (SEQ ID NO: 92), these data suggested that AptA might bind to multiple SH3 domains in yeast. We performed a systematic Y2H interaction matrix between AptA and all 28 yeast SH3 domains. The proteomic SH3 matrix shows that AptA is highly specific for Sho1 SH3, while other peptide aptamers isolated in the initial screen show some degree of cross-reactivity (FIG. 10). For example, both AptA and Pep05, which contain a leucine at position −5, are highly specific for Sho1 SH3. In contrast, Pep32, which has a proline instead of a leucine at position −5, shows weak affinity for two other yeast SH3 domains, (Lsb1 and Cdc25). The high specificity of AptA for the Sho1 SH3 domain indicates that the AptA dependent osmo-sensitive phenotype is Sho1 dependent and specific.

Intriguingly, a BLAST search of AptA against the yeast genome revealed significant homology to the yeast homologue of human Wiskott-Aldrich Syndrome protein, Las17, implicated in assembly and regulation of the actin cytoskeleton. Las17 has been shown to physically interact with the Sho1-SH3 domain but has not been placed in the HOG pathway. To examine whether AptA may exert its effect by disrupting a Las17p-Sho1 interaction, we asked whether overexpression of Las17 could overcome the effects of AptA expression. Surprisingly, control Δssk2/Δssk22 yeast cells over-expressing Las17 alone were not viable in the presence of osmotic stress. In contrast, wild type yeast over-expressing Las17 were viable. This suggests that Las17 functionally interacts with the Sho1 pathway. The osmo-sensitivity of Δssk2/Δssk22 GAL1/10::LAS17 cells may be caused by an ability of over-expressed Las17, like AptA, to compete with endogenous Pbs2 for Sho1-SH3 binding. An alternative possibility is that Las17 may be a negative regulator of the osmosensor Sho1. Finally, it is possible that Las17 is required early in the response for assembly of the Sho1/Pbs2 complex. Thus our data are consistent with the hypothesis that AptA inhibits PxxP mediated interactions between Pbs2 and the SH3 domain of Sho1, but perhaps also between Las17 and Sho1. We return to this question below.

Probing the Sequence Determinants of AptA Function

AptA and Apt32 differ by only three residues within the variable loop, at positions −6, −5 and +4 (Table II). Residues outside the core proline-rich motif have been shown to play important roles in determining the specificity and/or strength of binding of proline-rich peptides to SH3 domains. We mutated the three unique residues of Apt32 to the corresponding residues of AptA (Table III). Analysis of the 6 possible combinations of mutations revealed that a leucine residue at position −5 in AptA is the sole determinant of inhibitory activity in the osmo-resistance assay. When the −5 position in Apt32 is substituted by leucine, the peptide aptamer becomes inhibitory (mutant number 2, Table III). The addition to this leucine of the other residues from Apt32 did not prevent inhibition of Sho1 signalling by AptA, indicating that the residues at positions −6 and +4 are not crucial for activity. Schreiber and colleagues have previously established the structural basis for the role of residue side chains in determining affinity and specificity of the PPII/SH3 domain interaction. Our data indicate that while the identity of the residue at −6 may contribute to specificity in other polyproline II helix/SH3 domain interactions, in the case of the Pbs2/Sho1 SH3 interaction it is position −5 that probably plays a key role. This is the reverse of the situation studied by Feng et al [Feng S, Kasahara C, Rickles R J, Schreiber S L. 1995. Specific interactions outside the proline-rich core of two classes of Src homology 3 ligands. *Proc Nall Acad Sci USA.* 92: 12408-15.] and suggests that the mechanistic details of PPII/SH3 domain interactions may differ, despite the high degree of sequence conservation. This is consistent with the observation that the SH3 domain of Src selects for specific residues at positions −7 and −6, while Fyn SH3 selects at −6 and −5. In fact, we observed no selection at position −6, as the Sho1 SH3 accepted the following dipeptides at the −5 and −6 position: RL (AptA); LP (Pep32); SV (Apt34); VE (Apt40); PA (Apt94); RG (Apt124); DL (Apt03) and NL (Apt05), with the only conservation being the appearance of a leucine residue at the same position in 3 peptides (AptA, Apt03 and Apt05) and an arginine residue in 2 others (AptA and Apt124).

We noted that other peptides containing a leucine at −5 (such as Apt03 and 05) were not inhibitory. Unlike AptA, these two peptide aptamers are constrained. To test the idea that constraint prevents the PPII helix of peptide aptamers such as Apt03 and 05 from productive interaction with Sho1 SH3, we replaced the C-terminal stop codon of AptA with codons encoding each amino acid residue in turn to make AptA a full-length peptide aptamer constrained in STM. After re-constraint, only one of the seven amino acid residues P, V, C, D, H, F and W at +5 allow binding to Sho1 SH3 in the context of a constrained protein (Table IV). This contrasts with the findings of Feng et al [Feng S, Chen J K, Yu H, Simon J A, Schreiber S L. 1994. Two binding orientations for peptides to the Src SH3 domain: development of a general model for SH3-ligand interactions. *Science.* 266: 1241-7] and Rickles et al [Rickles R J, Botfield M C, Zhou X M, Henry P A, Brugge J S, Zoller M J. 1995. Phage display selection of ligand residues important for Src homology 3 domain binding specificity. *Proc Natl Acad Sci USA.* 92: 10909-13], who found that in the context of a free peptide this position tended towards aliphatic residues (A, S, P, V, L, R or Y; summarized in Table I). In addition, none of the constrained AptA variants show the ability to inhibit Pbs2-Hog1 activation (Table IV). These data are again consistent with the idea that the PPII helix needs to be conformationally unconstrained for tight binding to occur. They further indicate that in the context of STM, the presence of one of the 7 permissive residues at position +5 either allows the formation of a left handed type II polyproline helix or allows interaction at a surface on Sho1 distinct from the SH3 domain.

Restoration of Signaling Pathways by Peptide Aptamer Modules

Cellular signaling pathways are relayed by domain modules which wire or connect signaling components. For instance, the osmotic stress signal sensed by Sho1 is relayed by the recruitment of Pbs2 via the PxxP motif to the SH3 domain. Pbs2 both serves as a scaffold, recruiting the MAPKKK Ste11 to Sho1, and as a transmitter of the signal, being the MAPKK that activates Hog 1 MAPK. The evidence that Pbs2 functions as a scaffold is that mutation of the PxxP motif of Pbs2 to create pbs2 AxxA leads cells to activate the mating MAPK pathway (which shares Ste11 with the osmo-sensing pathway) on high osmolarity medium. The model is that activation of Ste11, whether by osmotic stress or mating pheromone, has the potential to activate the HOG or the mating pathway, and signalling specificity is conferred by the appropriate scaffold, Pbs2 in the HOG pathway and Ste5 in the mating pathway. The simplest explanation for the effect of AptA was that it competes for the recruitment of Pbs2 to Sho1, preventing binding and activation of the PxxP containing Pbs2. If this were true, and the simple scaffold model correct, then 1) cells expressing AptA may activate the mating cascade in response to osmotic shock and 2) it might be possible to bypass the recruitment of Pbs2 to Sho1 by tethering Ste11 directly to Sho1, if Ste11 and Pbs2 are constitutively bound to each other. However, we were unable to demonstrate activation of either of the mating MAP kinases, Fus3 or Kss1, in cells expressing AptA. In addition, targeting of Ste11 to Sho1 using a fusion of AptA to Ste11 was unable to restore Hog1 activation in cells expressing the AxxA mutant pbs2: Δssk2/Δssk2/Δpbs22 yeast expressing pbs2 AxxA and the Ste11-AptA fusion were inviable on high osmolarity plates (FIG. 14A), and Hog1 was not activated in these cells (FIG. 14C). This suggests that either the Ste11-AptA chimera was not capable of being activated upon NaCl treatment or that this fusion could not form a functional complex with Pbs2 MAPKK. An alternative explanation, uncovered by our implication of Las17 in the pathway, is that the Ste11-AptA fusion may restore the Pbs2/Sho1 complex, but is not able to substitute for the interaction with Las17. We next asked whether AptA could restore signalling from Sho1 to pbs2 AxxA that was defective for Sho1 binding. Indeed, fusion of AptA to the double AxxA mutant of Pbs2 restored signalling, and yeast cells were rescued from osmotic stress (FIG. 11). This result is consistent with AptA being able to mediate interaction between the AxxA mutant Pbs2 and Sho1-SH3. Conversely, introduction of the AxxA mutation into AptA abolished its interaction with Sho1-SH3 (FIG. 10, "A*"), strongly indicating that AptA is binding to Sho1 SH3 domain in these experiments. These data further demonstrate that any role played by Las17 would have to be upstream of formation of the Pbs2/Sho1 interaction, most likely at the plasma membrane, as the AptA-pbs2AxxA fusion is sufficient to restore the cytoplasmic section of the signal transduction pathway.

Finally, in order to confirm the mechanism of action of AptA, we asked whether AptA expression could disrupt the formation of a signalling complex in osmotically stressed cells. In these conditions, the complex between Sho1 and Pbs2 recruits Hog1. Accordingly, whole cell lysates from stressed yeast cells expressing AptA or STM (empty scaffold) were incubated with purified GST-Sho1 SH3. In the presence of AptA, the level of Hog1 in the Sho1-SH3 pull-down was decreased (FIG. 12). These observations are consistent with a mechanism of action of AptA where perturbation of the Pbs2-Sho1 interaction by AptA diminishes recruitment of Hog1 to the complex.

In sum, our experiments show that a signaling pathway can be disconnected and reconnected by peptide aptamer modules. Furthermore, our findings also suggest the importance of a direct interaction between Sho1 and Pbs2 in the HOG pathway which cannot be substituted in a simple manner by interaction between Sho1 and Ste11. However, Zarrinpar et al [Zarrinpar A, Bhattacharyya R P, Nittler M P, Lim W A. 2004. Sho1 and Pbs2 act as coscaffolds linking components in the yeast high osmolarity MAP kinase pathway. *Mol Cell.* 14: 825-32] have recently shown that interaction between Sho1 and Ste11 can allow signal transduction to occur in the absence of Pbs2, albeit to the mating rather than the osmo-sensing pathway. Thus, our data and those of Zarrinpar et al support a model where a very precise orientation of Sho1 and Ste11 relative to each other and probably to the accessory kinase Ste20 in a complex is required for signal transduction to occur.

Discussion

Peptide aptamers find application as tools to study proteins in the intracellular context, in health and in diseases. To fulfil this potential requires a robust and biologically neutral scaffold, and the ability to be able to demonstrate unequivocally that any phenotype observed in cells expressing a peptide aptamer is caused by its effect on the target protein. The goals of this study were to demonstrate the utility of our preferred scaffold, STM, for the presentation of highly specific peptide aptamers that could interfere with protein function in cells. We wished first, to ask whether we could create functional libraries of peptide aptamers comprising polyproline II helix peptides that had been identified by phage display as binding to SH3 domains. This was designed to challenge the ability of the scaffold to present peptides with the necessary specificity to discriminate between closely related SH3 domains and allowed us to explore the determinants of specificity and affinity for the SH3 domain/PxxP interaction in the context of a full length protein. Second, we wished to ask to what degree a peptide aptamer would allow us to explore a protein's biology in the cellular context.

Peptide Aptamers to Explore PxxP/SH3 Domain Interactions:

Previous studies of SH3 domains showed that they recognise ligand peptides containing a PxxP motif (where x is any residue) that can form a left-handed type II polyproline helix. These studies, which typically used phage display of libraries of free peptides 10-12 residues in length, defined both the ligand consensus motif and residues important for determining binding specificity and binding affinity. Using the numbering system of Yu et al [Yu H, Chen J K, Feng S, Dalgarno D C, Brauer A W, Schreiber S L. 1994. Structural basis for the binding of proline-rich peptides to SH3 domains. *Cell.* 76: 933-45], where the first proline of the PxxP motif is given the number "0", the preceding residue is "−1" and the following residue is "+1", it was shown that an arginine or a lysine residue at position −2 was important, and that the identity of the residue at position −5 is crucial for determining affinity and specificity. Structural analysis showed that residues at positions −1 and 0 fit into one pocket of the SH3 domain, residues at +2 and +3 in another. A third pocket, which is less well conserved between SH3 domains, is likely to determine specificity and affinity of binding, and makes contacts with residues at −6, −5, −4 and −3. Using a library of proline-anchored peptides 12 residues in length, presented and in theory constrained by our preferred scaffold protein, STM, we found a strong selection pressure against constrained peptides. The binders comprised either peptides presented at the carboxy-terminus of a prematurely truncated scaffold protein, or peptides greater than 24 residues in length that can reasonably be assumed to be less well constrained than the original 12 mer. Both classes of peptides are the result of rare events. Multimeric peptides result from the self-ligation of the encoding oligonucleotides prior to their ligation into the host plasmid. Truncated peptides are the result of either the presence of a stop codon in the encoding oligonucleotides or the mis-synthesis of the oligonucleotides used to encode the peptide library. Our library oligonucleotides was constructed using the codon "NNK", where N is any nucleotide and K is G or T. This library encodes all possible amino acids using 30 coding codons (one each for F, I, M, Y, H, Q, N, K, D, E and C; two each for V, S, P. T, A; and 3 each for L and R) and only one stop codon. In other words, the likelihood of an in-frame stop codon at any given position is 1/31, and the probability of obtaining a stop codon at the end of the coding region of the peptide is $0.03^{12}=5\times 10-8$. Our data are consistent with a model where the scaffold is able to conformationally constrain a 12 mer peptide to either prevent formation of a polyproline II helix, or to prevent the adoption by this helix of an extended conformation that would allow all the residue side chains to make appropriate contacts with the target SH3 domain. This would explain why peptide aptamers such as Apt32 are able to bind the Sho1 SH3, but not sufficiently tightly to inhibit binding. Our data therefore provide strong support for the hypothesis that the interaction of proline-rich ligands with SH3 domains requires that the ligand be relatively unconstrained.

Peptide Aptamers as Tools to Dissect a Protein Protein Interaction Network:

Cellular signaling is regulated by protein-protein interactions. To maintain the fidelity of each signaling pathway, the interactions between signaling proteins need to be highly regulated. In addition to the "core members" of each linear pathway, many other proteins such as scaffold proteins or intracellular transporter proteins are also involved spatially and dynamically to ensure the specificity of signal transduction. Therefore, a detailed dissection of the protein-protein interaction network will help us to understand how cellular behavior is being regulated.

We have shown that a peptide aptamer can be a useful tool to extend studies from yeast genetics to an understanding of specific protein-protein interactions. For example, we show that AptA can both disconnect a signaling pathway, and reconnect a dysfunctional pathway by targeting mutant Pbs2 back to Sho1 (FIGS. 9 and 11). It is interesting that fusions of AptA to Ste11 did not restore signal transduction in cells expressing mutant Pbs2 (FIG. 14), as others had identified a region of Sho1 that was not required for interaction with Pbs2, but was required to maintain specificity of signaling, suggesting that it might interact with Ste11. Our data suggest either that this region of Sho1 interacts only indirectly with Ste11, perhaps via Ste20, or that AptA inhibits more than one protein-protein interaction at the Sho1 SH3 domain in cells. The strongest candidate for a second site interaction involves Las17, which our data suggest could play a key role in transmitting the osmotic stress signal, possibly via the cytoskeleton. The hypothesis that AptA also affects Las17 function, as overexpression of Las17 itself conferred osmo-sensitivity, is supported by the fact that this phenotype is consistent with the hypothesis.

We note that Las17 was not isolated in screens for genes that confer osmo-sensitivity. This highlights an advantage that agents that interfere with protein function in the cellular context have over genetic screens, ie that conditional phenotypes can be identified for essential genes, and that one function of a protein (such as osmo-sensing) can be isolated from others (such as maintenance of the integrity of the cytoskeleton) if the agent interferes with only one of several protein-protein interactions.

Since a peptide aptamer exhibits its effect at the protein level, it should be possible to use a peptide aptamer to identify the protein interactome of a target protein. As a proof-of-concept, we used a GST pull down strategy as a preliminary test of the ability to examine the ability of the peptide aptamer to disrupt a protein complex. Expression of a peptide aptamer that is proposed to prevent the formation of the HOG1/Pbs2/Ste11 complex at the plasma membrane did indeed lead to a decrease in the presence of Hog1 protein at the cytoplasmic domain of Sho1p (FIG. 12). Hence, these data confirm the potential of using peptide aptamers to dissect physical protein-protein interaction networks. Combined with their very high specificity, demonstrated here even for the potentially promiscuous interaction between an SH3 domain and a degenerate polyproline II peptide library, this work suggests that peptide aptamers can advantageously form the basis for a toolkit for the dissection of protein function in the context of cellular networks according to the present invention.

Significance

Expression microarrays have uncovered many gene products as being differentially expressed in disease. A protein that is uniquely expressed, or sometimes simply over-expressed in a disease setting, is a potential therapeutic target. RNAi is currently a technique of choice for the validation of such candidate drug targets. However, proteins participate in multiple sets of interactions within cells. In practice, this raises the possibility that "knock-down" techniques such as RNAi may affect more than one pathway, leading to misleading results. This means that many valid therapeutic targets may be wrongly dismissed when the RNAi phenotype does not match expectations. What is clearly lacking in the prior art is the ability to dissect a protein's partnerships in the context of living cells.

We show here that peptide aptamers advantageously provide a solution to this problem, as they have the potential to answer subtle questions about each one of a protein's interactions within cells in turn. First, we demonstrate that peptide aptamers are capable of exquisite specificity, showing that 3 related peptide aptamers can distinguish between 28 closely related SH3 domains. Second, we also find that the binding affinities of peptide aptamers can be such that they compete in vivo for protein-protein interactions. Thus, we identified an inhibitor of a stress-sensing pathway in yeast that prevented signal transmission to an effector complex, and showed that this inhibitor also prevented the assembly of this complex. Third, our data also suggest that peptide aptamers may enable the uncovering of a non-essential function of a protein (such as the generation or transmission of a stress signal) from essential interactions (such as the regulation of cyto-skeletal integrity) that are necessary for cell viability. The invention also finds application in the context of human cells.

Materials and Methods

Example 13

Shot SH3 Domain Screen

This screen was previously described in [Woodman R, Yeh J T-H, Laurenson S, Ko Ferrigno P. 2005. Design and validation of a neutral protein scaffold for the presentation of peptide aptamers *J Mol Biol.* 352: 1118-33]. Briefly, a Pbs2-based mini library was constructed by ligating the degenerate oligonucleotide "NNK SYG AAT AAG CCC CTA CCC BCT CTA CCC SYG NNK" (SEQ ID NO: 51) (N=A, T, C or G; K=G or T; S=C or G; Y=C or T; B=C, G or T) into RsrII digested pJG4.5 STM vector. This partially randomized oligonucleotide cassette encodes the peptide sequence X(L/V/P/A)N (K/R)PLP(P/S/A)LP (L/V/P/A)X (SEQ ID NO: 34), where X is any amino acid. The theoretical library complexity at the protein level is 38,400. Library screening and hit confirmation are described in Woodman et al (ibid).

Yeast Osmotic Resistance Assay

Yeast cells were transformed with various Sho1-SH3 peptide aptamer constructs. For spot assays, 10000 cells of each transformant were spotted onto selective plates with or without 1M NaCl, supplemented with glucose or galactose/raffinose. Yeast cells were also directly streaked onto plates with or without 1M NaCl. Cell growth was recorded 3-5 days later.

Preparation of Yeast Cell Lysates and Western Blotting

Yeast cells were lysed with 1×SDS sampling buffer and vortexed vigorously with 80 µl glass beads for 1 minute. Samples were incubated in a 95° C. heat block for 5 minutes then quickly quenched on ice. Samples were then briefly spun down and supernatants were collected in clean 1.5 ml centrifuge tubes and stored at 4° C. Western blots were performed according to standard protocols and probed with rabbit polyclonal pan Hog 1 antibody Y-118 (Santa Cruz) or NEB anti-phospho p38 (clone 28B10). To detect phsophorylated, active Hog1.

Cloning of 27 Yeast SH3 Domains

The 27 putative yeast SH3 domains were PCR amplified from yeast genomic DNA and cloned into EcoRI and XhoI sites of yeast pEG202 vector. Oligonucleotide primer sequences for PCR are available from PKF upon request. Each SH3 domain was selected according to the definition given in the NCBI database (www.ncbi.nlm.nih.gov).

TABLE I

| A. Semi-rational design of Peptide Aptamer Library | | | | | | | | | | | | |
|---|---|---|---|---|---|---|---|---|---|---|---|---|
| Position | | -6 | -5 | -4 | -3 | -2 | -1 | 0 | 1 | 2 | 3 | 4 | 5 |
| Wild type Pbs2 | (SEQ ID NO: 50) | | V | N | K | P | L | P | P | L | P | V |
| Library variable residues | (SEQ ID NO: 93) | X | V P L A | N | K R | P | L | P | P S A | L | P | P L A | X |

| B. Alignment to previously identified PPII helices | | | |
|---|---|---|---|
| Name | Sequence | | Source |
| RLP2 | RALPPLPRY | (SEQ ID NO: 52) | 20 |
| VSL12 | VSLARRPLPPLP | (SEQ ID NO: 53) | 21 |
| PBS2 | VNKPLPPLPV | (SEQ ID NO: 50) | |
| AptA | GPRL<u>NKPL</u>PSLPV | (SEQ ID NO: 54) | This study |
| Apt32 | GPLP<u>NKPL</u>PSLPL | (SEQ ID NO: 55) | This study |
| Src C + 5 - 1 | PPVPSL | (SEQ ID NO: 56) | 23 |
| Src C + 5 - 2 | PPVPSL | (SEQ ID NO: 56) | " |
| Src C = 5 - 3 | PPLPARPHP | (SEQ ID NO: 57) | " |
| Src C + 5 - 4 | PPLPTLLPS | (SEQ ID NO: 58) | " |
| Src C + 5 - 5 | PPLPTPPLH | (SEQ ID NO: 59) | " |
| Lyn C + 5 - 1 | PPLPLPPRL | (SEQ ID NO: 60) | 23 |
| Lyn C + 5 - 2 | PPLPLPPRT | (SEQ ID NO: 61) | " |
| Lyn C + 5 - 3 | PPLPLPPRH | (SEQ ID NO: 62) | " |
| Lyn C + 5 - 4 | PPLPLPPPH | (SEQ ID NO: 63) | " |
| Fyn C + 5 - 1 | PPLPLPPLT | (SEQ ID NO: 64) | 23 |
| Fyn C + 5 - 2 | PPLPSAPRV | (SEQ ID NO: 65) | " |
| Fyn C + 5 - 3 | PPLPVLSEP | (SEQ ID NO: 66) | " |
| Fyn C + 5 - 4 | PPLPTSTQP | (SEQ ID NO: 67) | " |

TABLE I-continued

| | | |
|---|---|---|
| Fyn C + 5 - 5 | PPLPHLPDS (SEQ ID NO: 68) | " |
| Fyn C + 5 - 6 | PPLPSYTSH (SEQ ID NO: 69) | " |
| Fyn C + 5 - 7 | PPLPVATHP (SEQ ID NO: 70) | " |
| Fyn C + 5 - 8 | PPLPSSLSR (SEQ ID NO: 71) | " |
| Fyn C + 5 - 9 | PPLPAPHAR (SEQ ID NO: 72) | " |
| Fyn C + 5 - 10 | PPLPTVASP (SEQ ID NO: 73) | " |

TABLE II

Sho1-SH3 domain binders from the screen. Fourteen binders, which comprised peptide sequences constrained by STM, are described (see above). The peptide sequences given here are for those peptide aptamers that are truncated at the C-terminus, whether by a stop codon encoded by the library oligonucleotide, or one that is present in an alternative reading frame of STM accessed by an oligonucleotide-encoded frameshift.

| | | |
|---|---|---|
| AptA: | GPRL<u>NKPLPSLPV</u>* | (SEQ ID NO: 54) |
| 032: | GPLP<u>NKPLPSLPL</u>* | (SEQ ID NO: 55) |
| 034: | GPSV<u>NKPLPSLPSLPVYGP</u>* | (SEQ ID NO: 74) |
| 040: | GPVE<u>NKPLPALPAVGP</u>* | (SEQ ID NO: 75) |
| 094: | GPA<u>NKPLPALPALGSAVE</u>* | (SEQ ID NO: 76) |
| 124: | GPRG<u>NKPLPALPL</u>* | (SEQ ID NO: 77) |

TABLE III

Combinations of mutations from Apt32 to AptA

| | Sequence | | Osmosensitivity |
|---|---|---|---|
| AptA: | R<u>L</u>NKPLPSL<u>PV</u>* | (SEQ ID NO: 30) | + |
| Apt32: | <u>LP</u>NKPLPSL<u>PL</u>* | (SEQ ID NO: 78) | − |
| #01: | RPNKPLPSLPL* | (SEQ ID NO: 79) | − |
| #02: | LLNKPLPSLPL* | (SEQ ID NO: 80) | + |
| #03: | LPNKPLPSLPV* | (SEQ ID NO: 81) | − |
| #23: | LLNKPLPSLPV* | (SEQ ID NO: 82) | + |
| #13: | RPNKPLPSLPV* | (SEQ ID NO: 83) | − |
| #12: | RLNKPLPSLPL* | (SEQ ID NO: 84) | + |

The three residues that vary between AptA (inhibitory) and Apt 32 (neutral) are underlined. 6 combinations of mutations made to replace residues in Apt32 with those found at the corresponding position in AptA are highlighted in bold.

TABLE IV

Replacing the stop codon of AptA by 20 amino acids

| Sequences | | Sho1-SH3 binding | Osmosensitivity |
|---|---|---|---|
| RLNKPLPSLPV* | (SEQ ID NO: 30) | + | + |
| RLNKPLPSLPVA | (SEQ ID NO: 94) | − | − |
| RLNKPLPSLPVC | (SEQ ID NO: 95) | + | − |
| RLNKPLPSLPVD | (SEQ ID NO: 96) | − | − |
| RLNKPLPSLPVE | (SEQ ID NO: 97) | − | − |
| RLNKPLPSLPVF | (SEQ ID NO: 98) | + | − |
| RLNKPLPSLPVG | (SEQ ID NO: 99) | − | − |
| RLNKPLPSLPVH | (SEQ ID NO: 100) | + | − |
| RLNKPLPSLPVI | (SEQ ID NO: 101) | − | − |
| RLNKPLPSLPVK | (SEQ ID NO: 102) | + | − |
| RLNKPLPSLPVL | (SEQ ID NO: 103) | − | − |
| RLNKPLPSLPVM | (SEQ ID NO: 104) | − | − |
| RLNKPLPSLPVN | (SEQ ID NO: 105) | + | − |
| RLNKPLPSLPVP | (SEQ ID NO: 106) | + | − |
| RLNKPLPSLPVQ | (SEQ ID NO: 107) | − | − |
| RLNKPLPSLPVR | (SEQ ID NO: 108) | − | − |
| RLNKPLPSLPVS | (SEQ ID NO: 109) | − | − |
| RLNKPLPSLPVT | (SEQ ID NO: 110) | − | − |
| RLNKPLPSLPVV | (SEQ ID NO: 111) | + | − |
| RLNKPLPSLPVW | (SEQ ID NO: 112) | + | − |
| RLNKPLPSLPVY | (SEQ ID NO: 113) | − | − |
| RLNKPLPSLPVG*[a] | (SEQ ID NO: 114) | + | − |

*= Stop codon
[a] RLNKPLPSLPVG* (SEQ ID NO: 114) construct is a control peptide aptamer showing that the loss of inhibitory effect is due the constraint instead of the addition of extra residue after the $V_{+4}$ position.

All publications mentioned in this document are hereby incorporated by reference.

The invention claimed is:

1. An isolated scaffold polypeptide comprising the amino acid sequence shown as SEQ ID NO: 1.

2. An isolated polypeptide comprising the amino acid sequence shown as SEQ ID NO: 1, wherein amino acids 71-73 of SEQ ID NO: 1 are replaced by a peptide of 36 amino acids or fewer.

3. An isolated polypeptide comprising the amino acid sequence RLNKPLPSLPV (SEQ ID NO: 30).

4. A pharmaceutical composition comprising the isolated polypeptide of claim 3 and a pharmaceutically acceptable carrier.

5. The pharmaceutical composition of claim 4, wherein said isolated polypeptide consists of the amino acid sequence RLNKPLPSLPV (SEQ ID NO: 30).

* * * * *

SEQUENCE LISTING

<160> NUMBER OF SEQ ID NOS: 124

<210> SEQ ID NO 1
<211> LENGTH: 98
<212> TYPE: PRT
<213> ORGANISM: Homo sapiens

<400> SEQUENCE: 1

```
Met Ile Pro Trp Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Asp
        35                  40                  45

Ala Gly Thr Asn Tyr Tyr Ile Lys Val Arg Ala Gly Asp Asn Lys Tyr
    50                  55                  60

Met His Leu Lys Val Phe Asn Gly Pro Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe
```

<210> SEQ ID NO 2
<211> LENGTH: 98
<212> TYPE: PRT
<213> ORGANISM: Homo sapiens

<400> SEQUENCE: 2

```
Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe
```

<210> SEQ ID NO 3
<211> LENGTH: 70
<212> TYPE: PRT
<213> ORGANISM: Homo sapiens

<400> SEQUENCE: 3

```
Met Ile Pro Trp Gly Leu Ser Glu Ala Lys Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Asp
        35                  40                  45
```

```
Ala Gly Thr Asn Tyr Tyr Ile Lys Val Arg Ala Gly Asp Asn Lys Tyr
 50                  55                  60

Met His Leu Lys Val Phe
 65                  70

<210> SEQ ID NO 4
<211> LENGTH: 25
<212> TYPE: PRT
<213> ORGANISM: Homo sapiens

<400> SEQUENCE: 4

Pro Gly Gln Asn Glu Asp Leu Val Leu Thr Gly Tyr Gln Val Asp Lys
 1               5                  10                  15

Asn Lys Asp Asp Glu Leu Thr Gly Phe
            20                  25

<210> SEQ ID NO 5
<211> LENGTH: 106
<212> TYPE: PRT
<213> ORGANISM: Homo sapiens

<400> SEQUENCE: 5

Met Ile Pro Trp Gly Leu Ser Glu Ala Lys Pro Ala Thr Pro Glu Ile
 1               5                  10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Asp
         35                  40                  45

Ala Gly Thr Asn Tyr Tyr Ile Lys Val Arg Ala Gly Asp Asn Lys Tyr
     50                  55                  60

Met His Leu Lys Val Phe Asn Gly Pro Asp Thr Tyr Arg Tyr Ile Gly
 65                  70                  75                  80

Pro Pro Gly Gln Asn Glu Asp Leu Val Leu Thr Gly Tyr Gln Val Asp
                 85                  90                  95

Lys Asn Lys Asp Asp Glu Leu Thr Gly Phe
            100                 105

<210> SEQ ID NO 6
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ccggaattcc catgatacct ggaggc                                      26

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
atctcaaaag cccgtcagct cg                                          22

<210> SEQ ID NO 8
<211> LENGTH: 38
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 8
cttgaaagta ttcaacggac cgcccggaca aaatgagg                              38

<210> SEQ ID NO 9
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ggaattccac catgatacct ggaggcttat ct                                   32

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gctctagagc aaagcccgtc agctcgtcat                                      30

<210> SEQ ID NO 11
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggaattccac catgatacct tggcttatct gaggccaaac c                         41

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gctctagagc aaagcccgtc agctcgtcat                                      30

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggaattcacc atgccaaaaa agaagaaagg tagatatacc ttggggc                   47

<210> SEQ ID NO 14
<211> LENGTH: 30
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
gctctagagc aaagcccgtc agctcgtcat                                          30

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gactgactgg tccgccaaag aagaagagaa aggtaggtcc tcagtcagtc ag                 52

<210> SEQ ID NO 16
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ctgactgact gaggacc                                                        17

<210> SEQ ID NO 17
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccggaattca tgatacctgg aggcttatc                                           29

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ccggaattcc taaaagcccg tcagctcgtc                                          30

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
cagtataaaa ctcaagttga tgctggaaca aattac                                   36

<210> SEQ ID NO 20
<211> LENGTH: 27
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 20
ggcctcagat aagccccaag gtatcat                                          27

<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccggaattca tgatacctgg aggcttatc                                        29

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ccgctcgagc taaaagcccg tcagctcg                                         28

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
gtccggacac ctaccgctac atcg                                             24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtccgatgta gcggtaggtg tccg                                             24

<210> SEQ ID NO 25
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctgactgact gaggacc                                                     17

<210> SEQ ID NO 26
<211> LENGTH: 67
<212> TYPE: DNA
<213> ORGANISM: Artificial Sequence
```

```
<220> FEATURE:
<223> OTHER INFORMATION: Description of Artificial Sequence: Synthetic
      primer
<220> FEATURE:
<221> NAME/KEY: modified_base
<222> LOCATION: (15)..(16)
<223> OTHER INFORMATION: a, c, t or g
<220> FEATURE:
<221> NAME/KEY: modified_base
<222> LOCATION: (48)..(49)
<223> OTHER INFORMATION: a, c, t or g

<400> SEQUENCE: 26
gactgactgg tccgnnksyg aatargcccc tacccbctct acccsygnnk ggtcctcagt      60
cagtcag                                                               67

<210> SEQ ID NO 27
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cgaattcccg ggtgatatcg gtgatgataa tttcatttac                            40

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ataagaatgc ggccgcttaa cgatgcattt cttctggacc atc                        43

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaaagtattc aacggtccgc ccggacaaaa tg                                    32

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Leu Asn Lys Pro Leu Pro Ser Leu Pro Val
1               5                   10

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 31

Pro Lys Lys Lys Arg Lys Val
1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Thr Tyr Arg Tyr Ile
1               5

<210> SEQ ID NO 33
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Asn Lys Pro Leu Pro Pro Leu Pro Leu Val
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any naturally occurring amino acid
<220> FEATURE:
<221> NAME/KEY: MOD_RES
<222> LOCATION: (2)..(2)
<223> OTHER INFORMATION: Leu, Val, Pro or Ala
<220> FEATURE:
<221> NAME/KEY: MOD_RES
<222> LOCATION: (4)..(4)
<223> OTHER INFORMATION: Lys or Arg
<220> FEATURE:
<221> NAME/KEY: MOD_RES
<222> LOCATION: (8)..(8)
<223> OTHER INFORMATION: Pro, Ser or Ala
<220> FEATURE:
<221> NAME/KEY: MOD_RES
<222> LOCATION: (11)..(11)
<223> OTHER INFORMATION: Leu, Val, Pro or Ala
<220> FEATURE:
<221> NAME/KEY: MOD_RES
<222> LOCATION: (12)..(12)
<223> OTHER INFORMATION: Any naturally occurring amino acid

<400> SEQUENCE: 34

Xaa Xaa Asn Xaa Pro Leu Pro Xaa Leu Pro Xaa Xaa
1               5                   10

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (3)..(3)
<223> OTHER INFORMATION: Any naturally occurring amino acid
<220> FEATURE:
<221> NAME/KEY: MOD_RES
<222> LOCATION: (4)..(4)
<223> OTHER INFORMATION: Leu, Val, Pro or Ala
<220> FEATURE:
<221> NAME/KEY: MOD_RES
<222> LOCATION: (6)..(6)
<223> OTHER INFORMATION: Lys or Arg
<220> FEATURE:
<221> NAME/KEY: MOD_RES
<222> LOCATION: (10)..(10)
<223> OTHER INFORMATION: Pro, Ser or Ala
<220> FEATURE:
<221> NAME/KEY: MOD_RES
<222> LOCATION: (13)..(13)
<223> OTHER INFORMATION: Leu, Val, Pro or Ala
<220> FEATURE:
<221> NAME/KEY: MOD_RES
<222> LOCATION: (14)..(14)
<223> OTHER INFORMATION: Any naturally occurring amino acid

<400> SEQUENCE: 35

Gly Pro Xaa Xaa Asn Xaa Pro Leu Pro Xaa Leu Pro Xaa Xaa Gly Pro
1               5                   10                  15

<210> SEQ ID NO 36
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gly Pro Val Pro Asn Lys Pro Leu Pro Ala Leu Pro Val Ile Gly Pro
1               5                   10                  15

Gly Val Asn Lys Pro Leu Pro Ala Leu Pro Ala His Gly Pro Ile Arg
            20                  25                  30

Asn Lys Pro Leu Pro Ser Leu Pro Ala Ser Gly Pro
        35                  40

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gly Pro Val Leu Asn Lys Pro Leu Pro Ser Leu Pro Val Met Gly Pro
1               5                   10                  15

Thr Pro Asn Lys Pro Leu Pro Pro Leu Pro Ala Ala Gly Pro
            20                  25                  30

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 38

Gly Pro Asp Leu Asn Lys Pro Leu Pro Ala Leu Pro Val His Gly Pro
1               5                   10                  15

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gly Pro Tyr Leu Asn Arg Pro Leu Pro Ser Leu Pro Ala Tyr Gly Pro
1               5                   10                  15

Trp Val Asn Arg Pro Leu Pro Ser Leu Pro Leu Ser Gly Pro
            20                  25                  30

<210> SEQ ID NO 40
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Pro Asn Leu Asn Lys Pro Leu Pro Ala Leu Pro Val Leu Gly Pro
1               5                   10                  15

<210> SEQ ID NO 41
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gly Pro Val Val Asn Lys Pro Leu Pro Ser Leu Pro Val Lys Gly Pro
1               5                   10                  15

Asp Val Asn Lys Pro Leu Pro Ser Leu Pro Ala Val Gly Pro
            20                  25                  30

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gly Pro Pro Asn Val Lys Pro Leu Pro Ala Leu Pro Leu Met Gly Pro
1               5                   10                  15

Leu Leu Asn Lys Pro Leu Pro Ala Leu Pro Leu Asp Gly Pro
            20                  25                  30

<210> SEQ ID NO 43
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
```

-continued

<400> SEQUENCE: 43

Gly Pro Asp Pro Asn Arg Pro Leu Pro Ser Leu Pro Val Thr Gly Pro
1               5                   10                  15

Tyr Leu Asn Lys Pro Leu Pro Ala Leu Pro Val Ser Gly Pro
            20                  25                  30

<210> SEQ ID NO 44
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gly Pro Met Leu Asn Lys Pro Leu Pro Ser Leu Pro Val Gly Gly Pro
1               5                   10                  15

Gly Leu Asn Lys Pro Leu Pro Ser Leu Pro Ala Ala Gly Pro
            20                  25                  30

<210> SEQ ID NO 45
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gly Pro Ile Leu Asn Lys Pro Leu Pro Ala Leu Pro Leu Arg Gly Pro
1               5                   10                  15

Asp Pro Asn Arg Pro Leu Pro Ala Leu Pro Val Thr Gly Pro
            20                  25                  30

<210> SEQ ID NO 46
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gly Pro Phe Pro Asn Lys Pro Leu Pro Ala Leu Pro Leu Thr Gly Pro
1               5                   10                  15

Val Leu Asn Arg Pro Leu Pro Pro Leu Pro Arg Asn Gly Pro
            20                  25                  30

<210> SEQ ID NO 47
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gly Pro Tyr Leu Asn Lys Pro Leu Pro Ser Leu Pro Leu Cys Gly Pro
1               5                   10                  15

Ser Val Asn Arg Pro Leu Pro Ala Leu Pro Asp Val Gly Pro
            20                  25                  30

```
<210> SEQ ID NO 48
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Pro Glu Pro Asn Lys Pro Leu Pro Ala Leu Pro Leu Thr Gly Pro
1               5                   10                  15

Val Leu Asn Arg Pro Leu Pro Pro Leu Pro Arg Asn Gly Pro
            20                  25                  30

<210> SEQ ID NO 49
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gly Pro Arg Met Asn Lys Pro Leu Pro Ser Leu Pro Leu Gly Gly Pro
1               5                   10                  15

Ala Met Asn Lys Pro Leu Pro Ala Leu Pro Leu Gln Gly Pro
            20                  25                  30

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Asn Lys Pro Leu Pro Pro Leu Pro Val
1               5                   10

<210> SEQ ID NO 51
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(2)
<223> OTHER INFORMATION: a, c, t or g
<220> FEATURE:
<221> NAME/KEY: modified_base
<222> LOCATION: (34)..(35)
<223> OTHER INFORMATION: a, c, t or g

<400> SEQUENCE: 51
nnksygaata agcccctacc cbctctaccc sygnnk                                   36

<210> SEQ ID NO 52
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 52

Arg Ala Leu Pro Pro Leu Pro Arg Tyr
1               5

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Val Ser Leu Ala Arg Arg Pro Leu Pro Pro Leu Pro
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Pro Arg Leu Asn Lys Pro Leu Pro Ser Leu Pro Val
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Pro Leu Pro Asn Lys Pro Leu Pro Ser Leu Pro Leu
1               5                   10

<210> SEQ ID NO 56
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Pro Pro Val Pro Ser Leu
1               5

<210> SEQ ID NO 57
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Pro Pro Leu Pro Ala Arg Pro His Pro
1               5

<210> SEQ ID NO 58
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 58

Pro Pro Leu Pro Thr Leu Leu Pro Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Pro Pro Leu Pro Thr Pro Pro Leu His
1               5

<210> SEQ ID NO 60
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Pro Pro Leu Pro Leu Pro Pro Arg Leu
1               5

<210> SEQ ID NO 61
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Pro Pro Leu Pro Leu Pro Pro Arg Thr
1               5

<210> SEQ ID NO 62
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Pro Pro Leu Pro Leu Pro Pro Arg His
1               5

<210> SEQ ID NO 63
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Pro Pro Leu Pro Leu Pro Pro Pro His
1               5
```

```
<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Pro Pro Leu Pro Leu Pro Pro Leu Thr
1               5

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Pro Pro Leu Pro Ser Ala Pro Arg Val
1               5

<210> SEQ ID NO 66
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Pro Pro Leu Pro Val Leu Ser Glu Pro
1               5

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Pro Pro Leu Pro Thr Ser Thr Gln Pro
1               5

<210> SEQ ID NO 68
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Pro Pro Leu Pro His Leu Pro Asp Ser
1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 69

Pro Pro Leu Pro Ser Tyr Thr Ser His
1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Pro Leu Pro Val Ala Thr His Pro
1               5

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Pro Leu Pro Ser Ser Leu Ser Arg
1               5

<210> SEQ ID NO 72
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Pro Leu Pro Ala Pro His Ala Arg
1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Pro Leu Pro Thr Val Ala Ser Pro
1               5

<210> SEQ ID NO 74
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Gly Pro Ser Val Asn Lys Pro Leu Pro Ser Leu Pro Ser Leu Pro Val
1               5                   10                  15

Tyr Gly Pro
```

```
<210> SEQ ID NO 75
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Pro Val Glu Asn Lys Pro Leu Pro Ala Leu Pro Ala Val Gly Pro
1               5                   10                  15

<210> SEQ ID NO 76
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Pro Ala Asn Lys Pro Leu Pro Ala Leu Pro Ala Leu Gly Ser Ala
1               5                   10                  15

Val Glu

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Gly Pro Arg Gly Asn Lys Pro Leu Pro Ala Leu Pro Leu
1               5                   10

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Leu Pro Asn Lys Pro Leu Pro Ser Leu Pro Leu
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Pro Asn Lys Pro Leu Pro Ser Leu Pro Leu
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 80

Leu Leu Asn Lys Pro Leu Pro Ser Leu Pro Leu
1               5                   10

<210> SEQ ID NO 81
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Leu Pro Asn Lys Pro Leu Pro Ser Leu Pro Val
1               5                   10

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Leu Leu Asn Lys Pro Leu Pro Ser Leu Pro Val
1               5                   10

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Pro Asn Lys Pro Leu Pro Ser Leu Pro Val
1               5                   10

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Leu Asn Lys Pro Leu Pro Ser Leu Pro Leu
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: Any amino acid

<400> SEQUENCE: 85

Arg Leu Asn Lys Pro Leu Pro Ser Leu Pro Val Xaa
1               5                   10
```

```
<210> SEQ ID NO 86
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Leu Ser Gln Arg Ser Thr Ser Thr Pro Asn Val His Met
1               5                   10

<210> SEQ ID NO 87
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Pro Ser Leu Ser Gln Arg Ser Thr Ser Thr Pro Asn Val His Met
1               5                   10                  15

Gly Pro

<210> SEQ ID NO 88
<211> LENGTH: 5
<212> TYPE: PRT
<213> ORGANISM: Homo sapiens

<400> SEQUENCE: 88

Gln Val Val Ala Gly
1               5

<210> SEQ ID NO 89
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (5)..(24)
<223> OTHER INFORMATION: Any amino acid
<220> FEATURE:
<221> NAME/KEY: MOD_RES
<222> LOCATION: (27)..(28)
<223> OTHER INFORMATION: Any amino acid
<220> FEATURE:
<223> OTHER INFORMATION: see specification as filed for detailed
      description of substitutions and preferred embodiments

<400> SEQUENCE: 89

Xaa Asn Gly Pro Xaa Xaa Xaa Xaa Xaa Xaa Xaa Xaa Xaa Xaa Xaa
1               5                   10                  15

Xaa Xaa Xaa Xaa Xaa Xaa Xaa Xaa Gly Pro Xaa Xaa
            20                  25

<210> SEQ ID NO 90
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
```

```
-continued

<400> SEQUENCE: 90

Pro Leu Pro Pro Leu Pro
1               5

<210> SEQ ID NO 91
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Pro Leu Pro Ala Leu Pro
1               5

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Pro Leu Pro Ser Leu Pro
1               5

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (2)..(2)
<223> OTHER INFORMATION: Val, Pro, Leu or Ala
<220> FEATURE:
<221> NAME/KEY: MOD_RES
<222> LOCATION: (4)..(4)
<223> OTHER INFORMATION: Lys or Arg
<220> FEATURE:
<221> NAME/KEY: MOD_RES
<222> LOCATION: (8)..(8)
<223> OTHER INFORMATION: Pro, Ser or Ala
<220> FEATURE:
<221> NAME/KEY: MOD_RES
<222> LOCATION: (11)..(11)
<223> OTHER INFORMATION: Pro, Leu or Ala
<220> FEATURE:
<221> NAME/KEY: MOD_RES
<222> LOCATION: (12)..(12)
<223> OTHER INFORMATION: Any amino acid

<400> SEQUENCE: 93

Xaa Xaa Asn Xaa Pro Leu Pro Xaa Leu Pro Xaa Xaa
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 94

Arg Leu Asn Lys Pro Leu Pro Ser Leu Pro Val Ala
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Leu Asn Lys Pro Leu Pro Ser Leu Pro Val Cys
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Arg Leu Asn Lys Pro Leu Pro Ser Leu Pro Val Asp
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Leu Asn Lys Pro Leu Pro Ser Leu Pro Val Glu
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Leu Asn Lys Pro Leu Pro Ser Leu Pro Val Phe
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Leu Asn Lys Pro Leu Pro Ser Leu Pro Val Gly
1               5                   10

<210> SEQ ID NO 100
<211> LENGTH: 12
<212> TYPE: PRT
<213> ORGANISM: Artificial Sequence
```

-continued

```
<220> FEATURE:
<223> OTHER INFORMATION: Description of Artificial Sequence: Synthetic
      peptide

<400> SEQUENCE: 100

Arg Leu Asn Lys Pro Leu Pro Ser Leu Pro Val His
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Leu Asn Lys Pro Leu Pro Ser Leu Pro Val Ile
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Leu Asn Lys Pro Leu Pro Ser Leu Pro Val Lys
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Arg Leu Asn Lys Pro Leu Pro Ser Leu Pro Val Leu
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Arg Leu Asn Lys Pro Leu Pro Ser Leu Pro Val Met
1               5                   10

<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Arg Leu Asn Lys Pro Leu Pro Ser Leu Pro Val Asn
1               5                   10
```

```
<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Arg Leu Asn Lys Pro Leu Pro Ser Leu Pro Val Pro
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Arg Leu Asn Lys Pro Leu Pro Ser Leu Pro Val Gln
1               5                   10

<210> SEQ ID NO 108
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Arg Leu Asn Lys Pro Leu Pro Ser Leu Pro Val Arg
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Arg Leu Asn Lys Pro Leu Pro Ser Leu Pro Val Ser
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Arg Leu Asn Lys Pro Leu Pro Ser Leu Pro Val Thr
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

-continued

<400> SEQUENCE: 111

Arg Leu Asn Lys Pro Leu Pro Ser Leu Pro Val Val
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Arg Leu Asn Lys Pro Leu Pro Ser Leu Pro Val Trp
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Arg Leu Asn Lys Pro Leu Pro Ser Leu Pro Val Tyr
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Arg Leu Asn Lys Pro Leu Pro Ser Leu Pro Val Gly
1               5                   10

<210> SEQ ID NO 115
<211> LENGTH: 139
<212> TYPE: PRT
<213> ORGANISM: Gallus gallus

<400> SEQUENCE: 115

Met Ala Gly Ala Arg Gly Cys Val Val Leu Leu Ala Ala Ala Leu Met
1               5                   10                  15

Leu Val Gly Ala Val Leu Gly Ser Glu Asp Arg Ser Arg Leu Leu Gly
            20                  25                  30

Ala Pro Val Pro Val Asp Glu Asn Asp Glu Gly Leu Gln Arg Ala Leu
        35                  40                  45

Gln Phe Ala Met Ala Glu Tyr Asn Arg Ala Ser Asn Asp Lys Tyr Ser
    50                  55                  60

Ser Arg Val Val Arg Val Ile Ser Ala Lys Arg Gln Leu Val Ser Gly
65                  70                  75                  80

Ile Lys Tyr Ile Leu Gln Val Glu Ile Gly Arg Thr Thr Cys Pro Lys
                85                  90                  95

Ser Ser Gly Asp Leu Gln Ser Cys Glu Phe His Asp Glu Pro Glu Met
            100                 105                 110

```
Ala Lys Tyr Thr Thr Cys Thr Phe Val Val Tyr Ser Ile Pro Trp Leu
            115                 120                 125

Asn Gln Ile Lys Leu Leu Glu Ser Lys Cys Gln
    130                 135
```

<210> SEQ ID NO 116
<211> LENGTH: 98
<212> TYPE: PRT
<213> ORGANISM: Homo sapiens

<400> SEQUENCE: 116

```
Met Met Cys Gly Ala Pro Ser Ala Thr Gln Pro Ala Thr Ala Glu Thr
1               5                   10                  15

Gln His Ile Ala Asp Gln Val Arg Ser Gln Leu Glu Glu Lys Glu Asn
            20                  25                  30

Lys Lys Phe Pro Val Phe Lys Ala Val Ser Phe Lys Ser Gln Val Val
            35                  40                  45

Ala Gly Thr Asn Tyr Phe Ile Lys Val His Val Gly Asp Glu Asp Phe
        50                  55                  60

Val His Leu Arg Val Phe Gln Ser Leu Pro His Glu Asn Lys Pro Leu
65                  70                  75                  80

Thr Leu Ser Asn Tyr Gln Thr Asn Lys Ala Lys His Asp Glu Leu Thr
                85                  90                  95

Tyr Phe
```

<210> SEQ ID NO 117
<211> LENGTH: 98
<212> TYPE: PRT
<213> ORGANISM: Homo sapiens

<400> SEQUENCE: 117

```
Met Ile Pro Gly Gly Leu Ser Glu Ala Lys Pro Ala Thr Pro Glu Ile
1               5                   10                  15

Gln Glu Ile Val Asp Lys Val Lys Pro Gln Leu Glu Glu Leu Thr Asn
            20                  25                  30

Glu Thr Tyr Gly Lys Leu Glu Ala Val Gln Tyr Lys Thr Gln Val Val
            35                  40                  45

Ala Gly Thr Asn Tyr Tyr Ile Lys Val Arg Ala Gly Asp Asn Lys Tyr
        50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe
```

<210> SEQ ID NO 118
<211> LENGTH: 103
<212> TYPE: PRT
<213> ORGANISM: Rattus norvegicus

<400> SEQUENCE: 118

```
Met Asp Pro Gly Thr Thr Gly Ile Val Gly Val Ser Glu Ala Lys
1               5                   10                  15

Pro Ala Thr Pro Glu Ile Gln Glu Val Ala Asp Lys Val Lys Arg Gln
            20                  25                  30

Leu Glu Glu Lys Thr Asn Glu Lys Tyr Glu Lys Phe Lys Val Val Glu
            35                  40                  45
```

```
Tyr Lys Ser Gln Val Val Ala Gly Gln Ile Leu Phe Met Lys Val Asp
        50                  55                  60

Val Gly Asn Gly Arg Phe Leu His Met Lys Val Leu Arg Gly Leu Ser
 65                  70                  75                  80

Gly Asp Asp Asp Leu Lys Leu Leu Asp Tyr Gln Thr Asn Lys Thr Lys
                    85                  90                  95

Asn Asp Glu Leu Thr Asp Phe
            100

<210> SEQ ID NO 119
<211> LENGTH: 98
<212> TYPE: PRT
<213> ORGANISM: Bos taurus

<400> SEQUENCE: 119

Met Ile Pro Gly Gly Leu Thr Glu Ala Lys Pro Ala Thr Ile Glu Ile
 1               5                  10                  15

Gln Glu Ile Ala Asn Met Val Lys Pro Gln Leu Glu Gly Lys Thr Asn
                20                  25                  30

Glu Thr Tyr Glu Glu Phe Thr Ala Ile Glu Tyr Lys Ser Gln Val Val
            35                  40                  45

Ala Gly Ile Asn Tyr Tyr Ile Lys Ile Gln Thr Gly Asp Asn Arg Tyr
        50                  55                  60

Ile His Ile Lys Val Phe Lys Ser Leu Pro Gln Gln Ser His Ser Leu
 65                  70                  75                  80

Ile Leu Thr Gly Tyr Gln Val Asp Lys Thr Lys Asp Asp Glu Leu Ala
                    85                  90                  95

Gly Phe

<210> SEQ ID NO 120
<211> LENGTH: 146
<212> TYPE: PRT
<213> ORGANISM: Homo sapiens

<400> SEQUENCE: 120

Met Ala Gly Pro Leu Arg Ala Pro Leu Leu Leu Leu Ala Ile Leu Ala
 1               5                  10                  15

Val Ala Leu Ala Val Ser Pro Ala Ala Gly Ser Ser Pro Gly Lys Pro
                20                  25                  30

Pro Arg Leu Val Gly Gly Pro Met Asp Ala Ser Val Glu Glu Glu Gly
            35                  40                  45

Val Arg Arg Ala Leu Asp Phe Ala Val Gly Glu Tyr Asn Lys Ala Ser
        50                  55                  60

Asn Asp Met Tyr His Ser Arg Ala Leu Gln Val Val Arg Ala Arg Lys
 65                  70                  75                  80

Gln Ile Val Ala Gly Val Asn Tyr Phe Leu Asp Val Glu Leu Gly Arg
                    85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
    130                 135                 140

Asp Ala
145
```

```
<210> SEQ ID NO 121
<211> LENGTH: 142
<212> TYPE: PRT
<213> ORGANISM: Homo sapiens

<400> SEQUENCE: 121

Met Met Trp Pro Met His Thr Pro Leu Leu Leu Thr Ala Leu Met
1               5                   10                  15

Val Ala Val Ala Gly Ser Ala Ser Ala Gln Ser Arg Thr Leu Ala Gly
            20                  25                  30

Gly Ile His Ala Thr Asp Leu Asn Asp Lys Ser Val Gln Cys Ala Leu
        35                  40                  45

Asp Phe Ala Ile Ser Glu Tyr Asn Lys Val Ile Asn Lys Asp Glu Tyr
    50                  55                  60

Tyr Ser Arg Pro Leu Gln Val Met Ala Ala Tyr Gln Gln Ile Val Gly
65                  70                  75                  80

Gly Val Asn Tyr Tyr Phe Asn Val Lys Phe Gly Arg Thr Thr Cys Thr
                85                  90                  95

Lys Ser Gln Pro Asn Leu Asp Asn Cys Pro Phe Asn Asp Gln Pro Lys
            100                 105                 110

Leu Lys Glu Glu Glu Phe Cys Ser Phe Gln Ile Asn Glu Val Pro Trp
        115                 120                 125

Glu Asp Lys Ile Ser Ile Leu Asn Tyr Lys Cys Arg Lys Val
    130                 135                 140

<210> SEQ ID NO 122
<211> LENGTH: 149
<212> TYPE: PRT
<213> ORGANISM: Homo sapiens

<400> SEQUENCE: 122

Met Ala Arg Ser Asn Leu Pro Leu Ala Leu Gly Leu Ala Leu Val Ala
1               5                   10                  15

Phe Cys Leu Leu Ala Leu Pro Arg Asp Ala Arg Ala Arg Pro Gln Glu
            20                  25                  30

Arg Met Val Gly Glu Leu Arg Asp Leu Ser Pro Asp Asp Pro Gln Val
        35                  40                  45

Gln Lys Ala Ala Gln Ala Ala Val Ala Ser Tyr Asn Met Gly Ser Asn
    50                  55                  60

Ser Ile Tyr Tyr Phe Arg Asp Thr His Ile Ile Lys Ala Gln Ser Gln
65                  70                  75                  80

Leu Val Ala Gly Ile Lys Tyr Phe Leu Thr Met Glu Met Gly Ser Thr
                85                  90                  95

Asp Cys Arg Lys Thr Arg Val Thr Gly Asp His Val Asp Leu Thr Thr
            100                 105                 110

Cys Pro Leu Ala Ala Gly Ala Gln Gln Glu Lys Leu Arg Cys Asp Phe
        115                 120                 125

Glu Val Leu Val Val Pro Trp Gln Asn Ser Ser Gln Leu Leu Lys His
    130                 135                 140

Asn Cys Val Gln Met
145

<210> SEQ ID NO 123
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide
```

-continued

```
<400> SEQUENCE: 123

Met Ile Pro Gly Gly Leu Ser Glu Ala Leu Pro Ala Thr Pro Glu Ile
1               5                   10                  15

Gln Glu Ile Val Asp Lys Val Lys Pro Gln Leu Glu Glu Lys Thr Asn
            20                  25                  30

Glu Thr Tyr Gly Lys Leu Glu Ala Val Gln Tyr Lys Thr Gln Val Val
        35                  40                  45

Ala Gly Thr Asn Tyr Tyr Ile Lys Val Arg Ala Gly Asp Asn Lys Tyr
    50                  55                  60

Met His Leu Lys Val Phe Lys Ser Leu Pro Gly Gln Asn Glu Asp Leu
65                  70                  75                  80

Val Leu Thr Gly Tyr Gln Val Asp Lys Asn Lys Asp Asp Glu Leu Thr
                85                  90                  95

Gly Phe

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 124

His His His His His His
1               5
```